United States Patent
Betrouni et al.

(10) Patent No.: US 12,232,843 B2
(45) Date of Patent: Feb. 25, 2025

(54) METHOD FOR EARLY PREDICTION OF NEURODEGENERATIVE DECLINE

(71) Applicants: INSTITUT NATIONAL DE LA SANTE ET DE LA RECHERCHE MEDICALE (INSERM), Paris (FR); UNIVERSITE DE LILLE, Lille (FR); CENTRE HOSPITALIER REGIONAL UNIVERSITAIRE DE LILLE, Lille (FR)

(72) Inventors: Nacim Betrouni, Lille (FR); Régis Bordet, Lille (FR)

(73) Assignees: INSTITUT NATIONAL DE LA SANTE ET DE LA RECHERCHE MEDICALE (INSERM), Paris (FR); UNIVERSITE DE LILLE, Lille (FR); CENTRE HOSPITALIER REGIONAL UNIVERSITAIRE DE LILLE, Lille (FR)

(*) Notice: Subject to any disclaimer, the term of this patent is extended or adjusted under 35 U.S.C. 154(b) by 659 days.

(21) Appl. No.: 16/977,980

(22) PCT Filed: Mar. 6, 2019

(86) PCT No.: PCT/EP2019/055510
§ 371 (c)(1),
(2) Date: Sep. 3, 2020

(87) PCT Pub. No.: WO2019/170711
PCT Pub. Date: Sep. 12, 2019

(65) Prior Publication Data
US 2021/0228079 A1    Jul. 29, 2021

(30) Foreign Application Priority Data
Mar. 7, 2018    (EP) .................... 18305244

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/4082* (2013.01);
(Continued)

(58) Field of Classification Search
CPC ............... G06T 7/0012; G06T 7/40; G06T 2207/20081; G06T 2207/20084;
(Continued)

(56) References Cited

U.S. PATENT DOCUMENTS

2007/0081707 A1* 4/2007 Sirohey ................. G16Z 99/00
                                                                              382/128
2010/0158337 A1* 6/2010 Burger ................... A61B 6/507
                                                                              382/131
(Continued)

FOREIGN PATENT DOCUMENTS

| CN | 103793908 A | * | 5/2014 | ......... G06T 7/0012 |
| WO | WO-2016040784 A2 | * | 3/2016 | ............ A61B 5/055 |
| WO | WO-2017011746 A1 | * | 1/2017 | ......... A61B 5/0042 |

OTHER PUBLICATIONS

Eva A. Zeestraten, Andrew J. Lawrence, Christian Lambert, Philip Benjamin, Rebecca L. Brookes, Andrew D. Mackinnon, Robin G. Morris, Thomas R. Barrick, Hugh S. Markus Neurology Oct. 2017, 89 (18) 1869-1876; DOI: 10.1212/WNL.0000000000004594 (Year: 2017).*

(Continued)

*Primary Examiner* — Aaron W Carter
*Assistant Examiner* — Courtney Joan Nelson
(74) *Attorney, Agent, or Firm* — WC&F IP

(57) ABSTRACT

The present invention relates to a method for predicting neurodegenerative decline and/or its severity for a patient,
(Continued)

especially of cognitive impairment (CI). Strokes and Parkinson's disease are frequently associated with occurrence of long-term cognitive impairment or dementia with still incompletely resolved mechanisms. The discovery of diagnostic and predictive biomarkers thus remains a major challenge. The method of the invention uses radiomics corresponding to texture features extracted from a plurality of previously-acquired medical brain images and correlated with previously-acquired clinical and/or biological data. A classifier is trained beforehand for learning these radiomics, and then operated on radiomics computed from at least one brain image of a patient to generate a score representative of its risks of neurodegenerative decline. By applying this method on a cohort of 160 MCI and non-MCI patients, the inventors show that MCI patients could be early predicted with a mean accuracy of 88%. In the same way, the method was able to discriminate very early stages of cognitive decline in a Parkinson's disease population of 100 patients.

26 Claims, 10 Drawing Sheets

(51) Int. Cl.
| | | |
|---|---|---|
| *G06T 7/00* | (2017.01) | |
| *G06T 7/10* | (2017.01) | |
| *G06T 7/40* | (2017.01) | |
| *G16H 30/40* | (2018.01) | |
| *G16H 50/20* | (2018.01) | |
| *G16H 50/30* | (2018.01) | |

(52) U.S. Cl.
CPC .......... *A61B 5/4088* (2013.01); *A61B 5/7246* (2013.01); *A61B 5/7267* (2013.01); *A61B 5/7275* (2013.01); *G06T 7/0012* (2013.01); *G06T 7/10* (2017.01); *G06T 7/40* (2013.01); *G16H 30/40* (2018.01); *G16H 50/20* (2018.01); *G16H 50/30* (2018.01); *A61B 2576/026* (2013.01); *G06T 2207/10088* (2013.01); *G06T 2207/30016* (2013.01)

(58) Field of Classification Search
CPC . G06T 2207/30016; G06T 2207/30004; G06T 7/10; G06T 2207/10088; A61B 5/0042; A61B 5/7264; A61B 5/4842; A61B 8/0808; A61B 5/4088; A61B 5/165; A61B 6/5217; A61B 8/5223; A61B 2576/026; A61B 5/0013; A61B 2503/08; A61B 6/501; A61B 1/000096; A61B 5/4064; A61B 5/4082; A61B 5/055; A61B 5/7246; A61B 5/7267; A61B 5/7275; G16H 50/20; G16H 50/30; G16H 30/40
See application file for complete search history.

(56) References Cited

U.S. PATENT DOCUMENTS

| | | | |
|---|---|---|---|
| 2010/0179415 | A1 | 7/2010 | Wenzel |
| 2012/0252062 | A1* | 10/2012 | Biskup ............... G01N 33/5094 435/39 |
| 2014/0086836 | A1* | 3/2014 | Burnham ........... G01N 33/6896 424/1.81 |
| 2014/0303487 | A1* | 10/2014 | James .................. G01R 33/483 600/420 |
| 2016/0307319 | A1* | 10/2016 | Miller .................... A61B 5/055 |

OTHER PUBLICATIONS

Machine translation of CN-103793908-A (Year: 2014).*

* cited by examiner

| Texture features | B34 Group | | | D7 Group | | | M1 Group | | | M2 Group | | |
|---|---|---|---|---|---|---|---|---|---|---|---|---|
| | Spearman coefficient | p-value | Post-hoc test p-value | Spearman coefficient | p-value | Post-hoc test p-value | Spearman coefficient | p-value | Post-hoc test p-value | Spearman coefficient | p-value | Post-hoc test p-value |
| Mean | -0.246 | 0.01 | 0.01 | -0.383 | 0.05 | 0.001 | -0.35 | 0.01 | 0.04 | -0.295 | 0.02 | 0.01 |
| STD | - | - | - | - | - | - | - | - | - | - | - | - |
| Skewness | -0.223 | 0.01 | 0.01 | -0.23 | 0.001 | 0.02 | -0.265 | 0.02 | 0.04 | -0.35 | 0.03 | 0.05 |
| Kurtosis | - | - | - | - | - | - | - | - | - | - | - | - |
| Homogeneity | - | - | - | - | - | - | - | - | - | - | - | - |
| Contrast | - | - | - | - | - | - | - | - | - | - | - | - |
| Entropy | - | - | - | - | - | - | - | - | - | - | - | - |
| Correlation | 0.28 | 0.01 | 0.001 | 0.32 | 0.01 | 0.01 | 0.60 | 0.007 | 0.03 | 0.44 | 0.02 | 0.04 |
| Variance | - | - | - | - | - | - | - | - | - | - | - | - |
| sum-average | 0.27 | 0.02 | 0.001 | 0.282 | 0.01 | 0.03 | 0.53 | 0.017 | 0.05 | 0.573 | 0.01 | 0.001 |
| inertia | - | - | - | - | - | - | - | - | - | - | - | - |

Fig. 5

METHOD FOR EARLY PREDICTION OF NEURODEGENERATIVE DECLINE

TECHNICAL FIELD

The present invention relates to a method for predicting risks of neurodegenerative decline, preferably of cognitive impairment, using at least a classifier and a plurality of previously-acquired medical images of one or more areas of the brain.

BACKGROUND ART

Each year around 17 million people suffer stroke worldwide, one-third of who are at risk of developing cognitive impairment (CI) and then dementia. Patients with low severity stroke (NIH Stroke Scale <5) have a risk of about 45% of developing a cognitive disorder within 6 months, affecting at least one area of the brain. Along with a rapidly growing incidence due to the aging of the population, it is estimated that about 10% of the patients under 45 are concerned and can be greatly impacted by stroke-related morbidity.

Parkinson's disease is the second most common neurodegenerative disease in France after Alzheimer's disease. It is also a major cause of disability in the elderly. Parkinson's disease rarely affects subject before the age of 45, but rather older subjects, with a peak around 70 years old: 1% of those over 65 are affected. In total, between 100,000 and 120,000 people are affected in France, and about 8,000 new cases occur each year. Given the aging of the population, the incidence of the disease is progressing. Cognitive deficits are common in Parkinson's disease, even in non-demented patients. The prevalence of mild cognitive impairment (MCI) in Parkinson's disease patients ranges from 20 to 50% and those patients have a higher risk of developing dementia.

Parkinson's disease is often associated with cognitive deficits which are, classically, categorized using the Movement Disorders Society criteria that define three profiles: cognitively intact patients, patients with cognitive impairments and patients with dementia. This classification does not allow the identification of milder cognitive phenotypes, such as patients with cognitive deficits without reaching the level of mild cognitive impairment. Early detection of such subtle cognitive alterations is a key step for the initiation of care strategies but it is particularly challenging since cognitive profiles are heterogeneous. Currently, the diagnosis is mainly based on clinical features.

The discovery of diagnostic or predictive biomarkers thus remains a major challenge in medicine. Stroke, in particular, is frequently associated with occurrence of long-term cognitive impairment or dementia with still incompletely resolved mechanisms. With the lack of efficient molecules and management strategies, research on neuro-protective drugs is accompanied by an interest to an early patient screening with the objective of treatment administration from the onset of degeneration, if possible even before the onset of symptoms.

In the field of cognitive disorders, whether of degenerative or vascular origin, the challenge thus lies in the discovery of early markers to highlight the beginning of the pathophysiological and evolutionary process. The main characteristics of neurodegenerative disorders consist in atrophy and the increased presence of neurofibrillary tangles and amyloid plaques. Medical imaging is a major tool in this context, providing with structural markers, as volume and shape, but does not often allow early prediction.

Volumetric approaches, mainly based on volumetric measurement of some brain structures such as the hippocampus or the quantification of white matter abnormalities, are conventionally used, the degeneration being accompanied by atrophies of different anatomical brain structures, but most often their detection is late at a time when the symptoms are already clinically detected. With a slow accumulation over time before clinical symptoms become apparent, the early diagnosis allowing the initiation of early treatment is still challenging.

In recent years, radiomics have been used as medical markers. It refers to an analysis involving the extraction of quantitative imaging features from radiological images with the intent of building descriptive and predictive models relating the features to medical outcome or phenotypes signatures. Images gray levels texture is indeed a rich source of information and a key component in image analysis and understanding. During the past decade, results from different studies have shown the ability of texture analysis algorithms to extract diagnostically meaningful information from multimodality medical images. Radiomics can be defined as the conversion of images to higher dimensional data and the subsequent mining of these data is used for improved decision support.

In the oncology field, the concept of radiomics is employed with some cutting edge results, as described for example in the applications CN 107220966, CN 104834943, CN 106683081, and WO 2006/114003. Radiomics appear as a powerful technique to improve knowledge in tumor biology. Indeed, radiogenomics analysis of some cancers specimens consists in a prognostic radiomic signature, capturing intra-tumor heterogeneity, associated with underlying gene-expression patterns. This outcome suggests that radiomics could identify a general prognostic phenotype of cancers, as shown in the article of Aerts H. et al. "*Decoding tumor phenotype by noninvasive imaging using a quantitative radiomics approach*", in Nat Commun 5:4006, 2014. Hence, it is becoming a full biomarker used for cancer detection, diagnosis, therapeutic strategy definition, prognosis inference and response prediction.

Patent application US 2010/179415 describes a diagnosis method based on the use of metabolic images. The diagnosis is directly based on of the voxel values which are related to the radioactive tracer uptake.

Patent application US 2016/307319 relates to an approach based on content-based image retrieval that compares target images to be classified to a set of learning source images. The targets are spatially registered to the sources and then parcelled and labelled. Ranking by comparing different images features, such as texture, is used to classify the images parcels.

International application WO 2017/011746 describes an approach for determining the medical condition of a patient exhibiting multiple disease states. The method combines multiple images (PET and MRI) and compares the patient individual images features, especially grey levels, to reference images stored in a database.

In the context of neuro-imaging, the better sensibility of texture features than volumes measurements on hippocampus are beginning to be highlighted.

Application CN 104881680 describes a method realizing, from medical images, an extraction of two-dimensional texture characteristics and three-dimensional morphological characteristics, and the fusion of these characteristics, using a SVM learning algorithm ("Support Vector Machine"), with the aim of early identification of MCI and Alzheimer's disease.

Application CN 102930286 discloses a method using texture features extracted from brain images and a SVM algorithm for detecting asymmetry of the brain indicating early signs of Alzheimer's disease or senile dementia.

International application WO 2015/106374 discloses a method for extracting multidimensional texture characteristics from images acquired by Magnetic Resonance (MR) images of the brain of persons suffering from Alzheimer's disease, of persons suffering from MIC or of unaffected elderly persons. A SVM algorithm is used to classify these characteristics, with the goal of establishing a predictive model for the early diagnosis of Alzheimer's disease.

Applications CN 104414636, CN 105809175 and CN 107145756 discuss the use of texture features and classification algorithms for, respectively, the detection of brain micro-hemorrhages, brain edemas, and the prediction of cerebral strokes.

There exists a need to further improve the early prediction of the risks of neurodegenerative decline, especially after a stroke or for Parkinson's disease patients, by using, among others tools, medical imaging.

DISCLOSURE OF THE INVENTION

The invention aims at least to achieve this goal by virtue of a method for predicting risks of neurodegenerative decline of a patient, preferably of cognitive impairment, based on at least one medical brain image and at least one clinical and/or biological data of said patient, and using at least a classifier, trained beforehand to learn texture features extracted from a plurality of previously-acquired medical images of one or more areas of the brain and correlated with previously-acquired clinical and/or biological data, the method comprising:
  extracting one or more texture features from said at least one brain image,
  correlating said one or more extracted texture features with said at least one clinical or biological data, and
  based at least on said one or more correlated features, operating the trained classifier on the at least one brain image to generate a score representative of the risks of neurodegenerative decline of the patient.

A further object of the invention is a method for training a classifier to learn features, using a plurality of previously-acquired medical images of one or more areas of the brain and previously-acquired clinical and/or biological data, the method comprising:
  extracting one or more texture features from the previously-acquired images,
  correlating said one or more extracted texture features with at least one clinical or biological data, and
  training the classifier to learn said correlated features.

The method according to the invention is based on the combination of several types of medical data, associating the texture features extracted from brain images to different clinical and biological data. The radiomics approach is thus explored more deeply and used more efficiently.

It makes it possible to quantify different dependencies between the gray levels of the images, combined with a large number of analysis data, and, by using a machine learning approach, to combine these heterogeneous data, leading to the construction of a predictive model to identify patients inclined to develop neurodegenerative decline and mild cognitive impairments. The texture features reveal the very preliminary and subtle changes of the brain structures toward a neurodegenerative decline.

The invention provides an effective biomarker and the construction of a method for predicting the occurrence of neurodegenerative decline, especially of post-stroke cognitive impairment, by detecting early signs of decline. This approach is more efficient than the known volumetric approach. Indeed, it allows the prediction of the risks of decline before the symptoms are clinically detected.

The invention thus offers early diagnosis of neurodegenerative decline, prognosis on the evolution of the patient's condition and allows therapeutic follow-up and assessment of treatment efficacy.

This method can be implemented also on the animal, with the possible sacrifice of the animal.

The steps of the methods of the invention are advantageously performed automatically. Human intervention of an operator or a doctor may not be necessary.

Clinical and Biological Data

The biological data preferably include blood biomarkers, preferably protein panel, metabolite panel or microRNA signature. In a variant or in combination, biological data include genomic information and/or histological data, as for example neural density.

The clinical data preferably include neuropsychological data, preferably data from neuropsychological tests, as Montreal Cognitive Assessment (MoCA) or Mini Mental State Examination (MMSE) scores. It is known that a significant correlation exists between the general cognition and extracted image texture parameters, for example from the hippocampus. The clinical data may include score(s) relating to the motor state assessment of the patient.

The clinical data may include neuropsychological data from tests chosen from the Movement Disorder Society-Unified Parkinson's disease Rating Scale (MDS-UPDRS, sections I-IV), the Hoehn and Yahr staging scale. the 17-item Hamilton Depression Rating Scale (HAMD), the Parkinson Anxiety Scale (PAS) the Lille Apathy Rating Scale (LARS), the Mattis dementia rating scale (Mattis DRS), the forward and backward digit span and the Symbol Digit Modalities Test (SDMT), the Trail Making Test (TMT, B/A ratio), the interference index of the Stroop word color test, and/or the word generation task, i.e. with single and alternating phonemic conditions.

The clinical data may include values measuring the volume of at least one brain structure at different moments, preferably acquired on patients 72 h after a stroke and six months after a stroke (M6 exam).

It is indeed well-known that brain impaired functioning and cognitive decline are associated with cerebral atrophy. The description of cerebral structures atrophy provides information about the pathogenesis of the neurodegenerative diseases and the contribution of each structure. Different morphological imaging studies investigated this issue and established diagnosis markers from the neocortex or the deep gray matter. Hippocampus appears as the most impacted cerebral structure by atrophy due to cognitive decline. Thanks to the invention, the relationship between texture features extracted from 72H MR images and the volume evolution between 72H and M6 exams can be explored by correlating the texture features and the ratio of the normalized volumes.

Correlation

The extracted texture features may be automatically correlated with clinical and/or biological data by using a statistical data modelling technique, preferably correlation, as the Pearson correlation, regression or the method called "one-way analysis of variance" (ANOVA).

Structures of Interest

The method according to the invention may be applied on different brain structures in parallel, preferably hippocampus, entorhinal cortex, *pallidum*, thalamus, putamen, amygdala, nucleus accumbens, and/or caudate. Traditionally, atrophy studies concern structures involved in the memory processes as the hippocampus, the entorhinal cortex and the amygdala, but one can assume that cognitive deterioration may impact different structures. Therefore, selecting more structures for extracting potentially biomarkers allows facilitating the prediction of this deterioration.

A sub-region may be considered for the extraction of the texture features of each structure by extracting a volume of interest, preferably from the structure center and comprising at least 9×9×9 voxels. Radiomics calculation may require segmentation of structures of interest, but do not require precise structures delineation. This allows the application of the invention to small image areas in biopsy mode, corresponding to down-sampled structure for features extraction and analysis, and allows eliminating the need for segmentation that is tedious when manual or imprecise when automatic. The computational complexity is thus decreased.

For computing the volume of one brain structure, left and right parts of the structure in each hemisphere are preferably segmented for obtaining two bilateral volumes, the volume of the structure being the sum of said bilateral volumes, normalized by the intracranial volume of the brain. The segmentation may be performed by using the Freesurfer software package, for example the 6.0 version, with the cross sectional pipeline and default parameters.

Texture Features

The texture features are advantageously automatically extracted from the images using image processing, especially by computing first order statistics, second order statistics, preferably extracted from the co-occurrence matrix, and/or fractal dimension.

The texture features may be extracted by considering the whole brain, only gray or white matter, or specific brain regions.

A grayscale texture analysis may be performed to characterize the links between voxels and detect low amplitude changes.

In a preferred embodiment of the invention, the texture features extracted from the images include model-based features, preferably the fractal dimension of the considered brain structure. The fractal dimension allows completing heterogeneity description of each anatomical structure, and offers the ability to describe the images complexity by characterizing similarities at different spatial resolutions.

The texture features extracted from the images may include first-order statistics, preferably the mean gray level, the standard deviation, the kurtosis and/or the skewness. Kurtosis is a measure of whether the data are heavy-tailed or light-tailed relatively to a normal distribution. Positive kurtosis indicates a peaked distribution while negative value indicates a flat distribution. Skewness quantifies the lack of symmetry, taking null values for a symmetric distribution and negative values for a lefty skewed data.

The texture features extracted from the images may include second-order statistics, preferably homogeneity, also called angular second moment, contrast, entropy, correlation between pixels, variance, also called sum of squares, sum average, inverse difference moment, and/or inertia. The second-order texture values are preferably computed from the co-occurrence matrix (GLCM), whose entries represent the number of times that intensity levels i and j occur in two voxels separated by the distance d in the direction a. In order to obtain a full neighborhood interaction, a matrix may be selected to cover the 26-connected directions of neighboring voxels in 3D space.

First-order statistics are mainly used to study the voxel values distribution without considering spatial relationships while second-order statistics describe the spatial relationships between the values.

Quantitatively-extracted descriptors of size, shape and surface of the anatomical structures may also be extracted.

The table below summarizes the considered texture features with their significance and the associated equations.

| Features | Description | Formulas |
|---|---|---|
| First order statistics | | |
| Mean | Mean image gray level values | |
| SD | Standard deviation of gray level values | |
| Kurtosis | Kurtosis is a measure of whether the data are heavy-tailed or light-tailed relatively to a normal distribution. Positive kurtosis indicates a peaked distribution while negative value indicates a flat distribution. | $Kurt = E\left[\left(\frac{X - \text{Mean}}{SD}\right)^2\right]$ |
| Skewness | Skewness quantifies the lack of symmetry. Nil for a symmetric distribution and negative values for a lefty skewed data. | $Skew = E\left[\left(\frac{X - \text{Mean}}{SD}\right)^2\right]$ |
| Second order statistics | | |
| Homogeneity | Homogeneity represents the uniformity of the texture intensity (a measure of the closeness of the distribution of elements in the co-occurrence matrix). | $Homogeneity = \sum_{i=0}^{G-1}\sum_{j=0}^{G-1}([P(i,j))^2$ |
| Contrast | Contrast represents the degree to which the texture intensity levels | $Constrast = \sum_{n=0}^{G-1}|i-j|^2\left\{\sum_{i=0}^{G}\sum_{j=0}^{G}(P(i,j)\right\}$ |

-continued

| Features | Description | Formulas |
|---|---|---|
| | differ between voxels or local intensity variation. Will favor contributions from the p(i,j) away from the diagonal. | $\|i - j\| = n$ |
| Entropy | Entropy represents the degree of uncertainty (measure of randomness). | $\text{Entropy} = -\sum_{i=0}^{G-1} \sum_{j=0}^{G-1} P(i,j) \cdot \log(P(i,j))$ |
| Correlation | Correlation represents the degree of mutual dependency between pixels | $\text{Correlation} = \sum_{i=0}^{G-1} \sum_{j=0}^{G-1} \frac{\{i \cdot j\} \cdot P(i,j) - \{\mu_x \cdot \mu_y\}}{\sigma_x \cdot \sigma_y}$ |
| Variance | Variance gives high weights for the elements different for the average value. | $\text{Variance} = \sum_{i=0}^{G-1} \sum_{j=0}^{G-1} (i = \mu)^2 P(i,j)$ |
| Sum Average | Sum Average measures the relationship between occurrences of pairs with lower intensity values and occurrences of pairs with higher intensity values. | $SumAvg = \sum_{I=0}^{2G-2} i \cdot P_{x+y}(i)$ |
| Inertia | Inertia measures the difference between the highest and the lowest values of a contiguous set of voxels. | $\text{Inertia} = \sum_{i=0}^{G-1} \sum_{j=0}^{G-1} \{i-j\}^2 \cdot P(i,j)$ |
| Inverse difference moment | get small contributions from inhomogeneous areas (i /= j). The result is a low InvDiff value for inhomogeneous images, and a relatively higher value for homogeneous images | $nvDiff = \sum_{i=0}^{G-1} \frac{P(i,j)}{1 + (i-j)^2}$ <br><br> $InvDiff = \sum_{i=0}^{G-1} \frac{P(i,j)}{1 + (i-j)^2}$ |

Where
G is the number of gray levels used.
i is the intensity value of a neighbor voxel and j the intensity value of a reference pixel.
P(i,j) is the probability of the appearance of the (i,j) pair in the co-occurrence matrix.
μ is the mean value of P
$P_x$ and $P_y$ are the marginal probabilities and $\sigma_x$, $\sigma_y$ are the STD of $P_x$ and $P_y$ respectively.

$P_{x+y} = \sum_{i=0}^{G-1} \sum_{j=0}^{G-1} P(i,j), i + j = k \text{ for } k = 0, 1 \ldots G-1$ Model based

| Fractal dimension | Quantify the global heterogeneity of a structure. Takes value in the interval [2,3]. More a structure is heterogeneous, the more its fractal dimension is close to 2. | $FD = \frac{\log(N_\partial)}{\log(1/\partial)}$ <br><br> where $N_\partial$ is the smallest number of sets of $\partial$ diameter needed to cover the structure |

Electronic System

Each step of the methods according to the invention may be carried out on an electronic system, in particular a personal computer, a calculation server or a medical imaging device, preferably comprising at least a microcontroller and a memory.

Brain Images

The brain images are preferably MR images, preferably T1W MR images. In this case, the images are anatomic and easy to obtain, and the acquisition does not require the use of a radioactive tracer.

In variants, the brain images are X-ray images or PET images ("positron emission tomography").

The brain images may be two-dimensional images or files of dimension higher than 2.

The brain images are obtained by non-invasive imaging techniques.

The previously-acquired brain images may have been acquired from patients with different neurodegenerative profiles, preferably from healthy patients and/or from patients after a stroke, preferably 72 h after a stroke, and/or at different moments from patients suffering from Parkinson's disease for showing its evolution.

The method for predicting risks of neurodegenerative decline according to the invention may comprise a preliminary step of acquisition of the brain images of the patient, using a medical imaging device. The acquisition of the images and the classification steps of the predicting method may be performed consecutively.

In a variant, the acquisition of the images and the classification steps of the predicting method are performed at different times. In this case, the brain images of the patient, already available, may have been stored on the memory of the electronic system.

Classification

By "classifier", it has to be understood a learning model with associated learning algorithms that analyze data, used for classification and regression analysis.

The classifier may be a support vector machine or a classification and regression tree (CART). This second method creates mutually exclusive classes by answering questions in a predefined order, while SVM is a supervised clustering method allowing building models by integrating a high number of variables that cannot be separated linearly. In this approach, similarity kernels are used for data transformation and for choosing data points or support vectors.

In a variant, the classifier is a neuronal network.

The brain images may be split into a training set and a test set. Each set advantageously includes images from patients with different neurodegenerative profiles.

Once the learning step is achieved, there is advantageously no need to access to an image database.

For both learning and classification steps, in the case where the classifier is a support vector machine, the texture features may be extracted for each brain structure and then some features are selected by using a Principal Components Analysis, a z-score normalization being preferably further applied to the selected features. By using this algorithm, the aim is to build a predictive model integrating all the radiomics features from all the considered anatomical structures. In order to limit the variables number, bilateral structures are advantageously no more considered separately and left and right sides are grouped. Applying a principal components analysis allows keeping only the most discriminant and uncorrelated features. This dimensionality reduction technique allows avoiding model over-fitting.

Based on the results of the classification by the trained classifier, a score representative of the risks for a patient to suffer from neurodegenerative decline is generated. Such risks may be evaluated at short term, especially in the next few months, for example between 6 months and 12 months. The classification according to the invention allows classifying patients in groups with respect to their neurodegenerative profile.

The score may be in the form of a probability for a patient for belonging to a predefined neurodegenerative profile, especially chosen from: healthy, mild risks of cognitive impairment, severe risks of neurodegenerative decline, quick evolution of Parkinson's disease, or a predefined cognitive profile.

Said predefined profiles are advantageously used during the learning step of the classifier, in order that the latter can learn to associate the correlated features with such profiles.

The score may be in the form of a numerical value, preferably evaluating the risks of neurodegenerative decline at short term, for example a value comprised between 0 and 10, the higher is the value, the higher are the risks.

In a variant, the score is in the form of a letter, especially showing that a patient is thought to belong to a group of people having a predefined neurodegenerative profile, for example group A, group B, group C, and so on.

Said score may be transmitted to a user by any suitable mean, for example by being displayed on a screen of the electronic system, printed, or by vocal synthesis.

Said score may be used as entry value in another program, and/or may be combined to other information, for example clinical and/or biological data.

Scores obtained for a same patient at different times may be compared in order to assess the evolution of its neurodegenerative decline. Successive classification scores may be stored on the memory of the electronic system.

Computer Program Product

A further object of the invention is a computer program product for predicting risks of neurodegenerative decline of a patient, preferably of cognitive impairment, based on at least one medical brain image and at least one clinical and/or biological data of said patient, and using at least a classifier, trained beforehand to learn texture features extracted from a plurality of previously-acquired medical images of one or more areas of the brain and correlated with previously-acquired clinical and/or biological data, the computer program product comprising a support and stored on this support instructions that can be read by a processor, these instructions being configured for:

- extracting one or more texture features from said at least one brain image,
- correlating said one or more extracted texture features with said at least one clinical or biological data, and
- based at least on said one or more correlated features, operating the trained classifier on the at least one brain image to generate a score representative of the risks of neurodegenerative decline of the patient.

The features defined above for the prediction method apply to the computer program product.

Image Processing Method

Yet another object of the invention is a method for processing medical brain images in order to predict risks of neurodegenerative decline of a patient, preferably of cognitive impairment, using at least a classifier, a plurality of previously-acquired medical images of one or more areas of the brain, and previously-acquired clinical and/or biological data, the method comprising the steps of:

- extracting one or more texture features from the previously-acquired images,
- correlating said one or more extracted texture features with at least one clinical or biological data, and
- training the classifier to learn said correlated features.

The method, being based on at least one medical brain image and at least one clinical and/or biological data of said patient, may further comprise:

- extracting one or more texture features from said at least one brain image,
- correlating said one or more extracted texture features with said at least one clinical or biological data, and
- based at least on said one or more correlated features, operating the trained classifier on the at least one brain image to generate a score representative of the risks of neurodegenerative decline of the patient.

The methods according to the invention may be carried out on a processor embedded on the medical imaging device used to acquire the brain images.

Said medical imaging device may be configured to display brain images of a patient and the associated classification score.

The features defined above for the prediction method apply to the image processing method.

DESCRIPTION OF THE DRAWING

The invention may be better understood from reading the following detailed description of non-limiting implementation examples thereof, and with reference to the attached drawing, in which:

FIG. 5 is a table summarizing results for Spearman correlation analyses between texture features and neural cells densities in the embodiment of FIG. 4.

DETAILED DESCRIPTION

Figure 1:
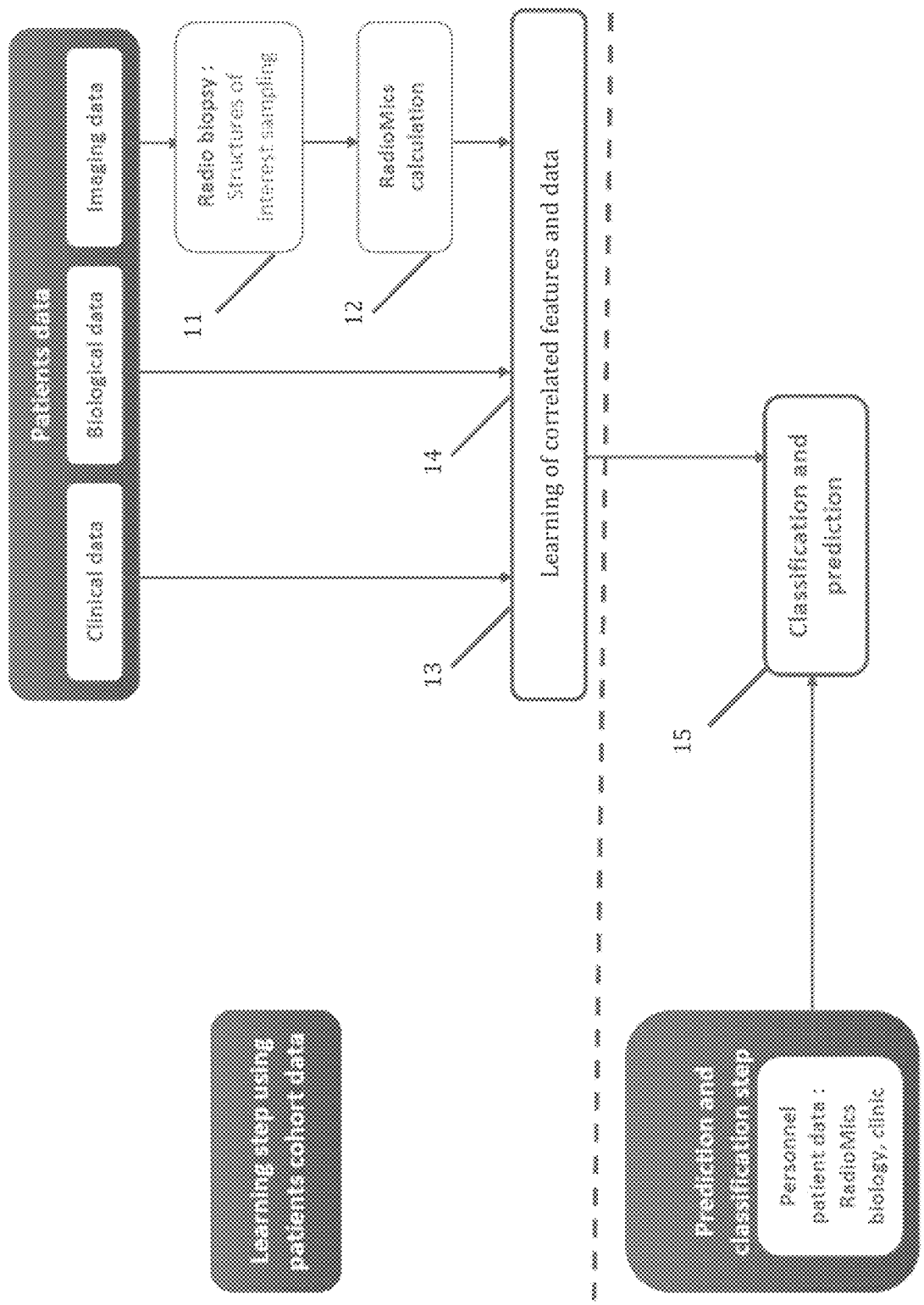
FIG. 1 is a block diagram showing some steps of the method according to the invention.

An example of detailed steps for predicting risks of neurodegenerative decline according to the invention will be described with reference to FIG. 1.

A learning step is beforehand performed, using patients cohort data, more precisely a plurality of previously-acquired medical images of one or more areas of the brain, and previously-acquired clinical and/or biological data. As described above, one or more texture features are extracted from the images, in a step 12.

The method of the invention is advantageously applied on different main brain structures in parallel, preferably hippocampus, entorhinal cortex, *pallidum*, thalamus, putamen, amygdala, nucleus accumbens, and/or caudate. In this embodiment, in a step 11, as shown in FIG. 1, sub-regions are considered for the extraction of the texture features of each structure by extracting a volume of interest, preferably comprising 9×9×9 voxels.

In this embodiment, the texture features extracted from the images include the fractal dimension of the considered brain structure, as well as first-order statistics, as mean, standard deviation, kurtosis and/or skewness, and second-order statistics, as homogeneity, contrast, entropy, correlation between pixels, variance, sum average, and/or inertia.

In a step 13, the extracted texture features are correlated with at least one clinical or biological data, by using in this example the Pearson correlation. A classifier is then trained to learn said correlated features in a further step 14.

The learned features are afterwards used to operate the trained classifier to classify at least one brain image of a patient in a prediction and classification step 15. To this end, one or more texture features are extracted from said at least one brain image, and said one or more extracted texture features are correlated with at least one clinical or biological data of the patient. Based on said correlated features, a score representative of the risks of neurodegenerative decline is generated.

All the steps described above are performed automatically on an electronic system, for example a personal computer, a calculation server or a medical imaging device.

Example 1: First Example for Post-Stroke Cognitive Impairment

As previously described, the biological data may include blood biomarkers, and/or genomic information, and/or histological data, while the clinical data may include data from neuropsychological tests, as MoCA in this example, and values measuring the volume of at least one brain structure at different moments, for example acquired on patients 72 h after a stroke and six months after a stroke.

In the considered embodiment, data from the STROK-DEM cohort (Study of Factors Influencing Post-stroke Dementia, from Clinicaltrials.gov with registration number NCT01330160) are used. This base collects clinical, biological, lesional and pharmacological data from stroke patients of different ages, with the aim of determining factors associated with post-stroke dementia. The study concerned patients with hemispheric stroke with a first MR exam dating from less than 72H with an IQ-code below 64 ("Informant questionnaire on cognitive decline") and clinical follow up at 6 (M6), 12 and 36 months.

In this embodiment, the previously-acquired brain images are acquired from healthy patients and from patients 72 h post-stroke, more precisely 3DT1W MR images with 1 mm3 voxel size acquired on a 3T MR machine. 90 patients were included in the study, among them 48 were diagnosed with cognitive impairment at M6 exam using neuropsychological assessment battery including in particular MoCA scores. M6 MR images were used to estimate the volume evolution of different anatomical brain structures between 72H and M6 exams.

For the training and the classification, the images are advantageously split into a training set and a test set, with, in this example, 70 images (38 MCI patients and 32 healthy, non MCI, patients) randomly assigned to the training set and the remaining 20 images (10 MCI and 10 non-MCI) assigned to the test set. The classifier is thus trained with texture features extracted from images of two patient profiles: with CI, without CI.

In this example, the classifier is a support vector machine, for example from the open source SVM library "LibSVM" (http://www.csie.ntu.edu.tw/~cjlin/libsvm).

The relevance of the texture features has been tested for the considered anatomical structures and the different texture features, by performing a statistical p-value analysis, where p-values less than 0.05 were considered to design significant differences. For both full anatomical brain structures and sub-regions of interest, the features are, in this example and preferably, compared using the method called "one-way analysis of variance" (ANOVA) to test differences between MCI and non-MCI patients. If the result indicated differences, a post hoc t-test was performed.

The results of the ANOVA analysis of the radiomics features and the corresponding p-values when differences are highlighted are summarized in the tables below (gray cells indicate when no significant differences are found). Except the standard deviation (SD), the first-order statistics parameters highlight significant differences for all the structures, as well as fractal dimension. For the second-order statistics, only entropy and correlation are significant for all the structures. The remaining parameters are significant for most of the structures.

|  | Mean | SD | Kurtosis | Skewness | Homog. | Contrast |
| --- | --- | --- | --- | --- | --- | --- |
| Left hippo. | p = 0.03 | p = 0.009 | p = 0.02 | p = 0.007 | p = 0.02 | p = 0.01 |
| Right hippo. | p = 0.02 | p = 0.007 | p = 0.03 | p = 0.006 | p = 0.03 | p = 0.008 |
| Left ent. cortex | p = 0.01 | p = 0.008 | p = 0.04 | p = 0.001 | p = 0.002 | p = 0.03 |
| Right ent. cortex | p = 0.01 | p = 0.01 | p = 0.001 | p = 0.02 | p = 0.01 | p = 0.01 |
| Left Thalamus | p = 0.01 | p = 0.02 | p = 0.02 | p = 0.01 | p = 0.02 | p = 0.009 |
| Right thalamus | p = 0.01 | P = 0.03 | p = 0.01 | p = 0.02 | p = 0.01 | p = 0.02 |
| Left Pallidum | p = 0.02 |  | p = 0.01 | p = 0.03 | p = 0.01 | p = 0.02 |
| Right Pallidum | p = 0.01 |  | p = 0.02 | p = 0.01 | p = 0.02 | p = 0.01 |
| Left Putamen | p = 0.03 | p = 0.02 | p = 0.03 | p = 0.02 | p = 0.03 | p = 0.04 |
| Right Putamen | p = 0.01 | p = 0.01 | p = 0.01 | p = 0.03 | p = 0.01 | p = 0.001 |
| Left amygdala | p = 0.02 |  | p = 0.03 | p = 0.02 |  |  |
| Right amygdala | p = 0.01 |  | p = 0.04 | p = 0.01 |  |  |
| Left nucl. acc. | p = 0.04 |  | p = 0.01 | p = 0.04 |  | p = 0.01 |
| Right nucl. acc. | p = 0.01 |  | p = 0.04 | p = 0.02 |  | p = 0.04 |
| Left caud. nuc. | p = 0.02 |  | p = 0.03 | p = 0.04 |  |  |
| Right caud. nuc. | p = 0.01 |  | p = 0.02 | p = 0.03 |  |  |

|  | Entropy | Correla. | Variance | Sum avg | Inertia | Frac. Dim |
| --- | --- | --- | --- | --- | --- | --- |
| Left hippo. | p = 0.006 | p = 0.02 | p = 0.03 | p = 0.007 | p = 0.009 | p = 0.003 |
| Right hippo. | p = 0.009 | p = 0.03 | p = 0.04 | p = 0.001 | p = 0.04 | p = 0.001 |
| Left ent. cortex | p = 0.02 | p = 0.01 | p = 0.009 | p = 0.01 | p = 0.02 | p = 0.01 |
| Right ent. cortex | p = 0.007 | p = 0.002 | p = 0.008 | p = 0.02 | p = 0.006 | p = 0.008 |
| Left Thalamus | p = 0.01 | p = 0.02 | p = 0.04 | p = 0.01 | p = 0.03 | p = 0.004 |
| Right thalamus | p = 0.01 | p = 0.01 | p = 0.03 | p = 0.02 | p = 0.02 | p = 0.009 |
| Left Pallidum | p = 0.03 | p = 0.01 |  | p = 0.003 | p = 0.01 | p = 0.01 |
| Right Pallidum | p = 0.03 | p = 0.02 |  | p = 0.008 | p = 0.04 | p = 0.01 |
| Left Putamen | p = 0.02 | p = 0.03 |  | p = 0.009 | p = 0.007 | p = 0.008 |
| Right Putamen | p = 0.02 | p = 0.01 |  | p = 0.03 | p = 0.03 | p = 0.01 |
| Left amygdala | p = 0.02 | p = 0.03 |  | p = 0.01 |  | p = 0.02 |
| Right amygdala | p = 0.01 | p = 0.04 |  | p = 0.01 |  | p = 0.01 |
| Left nucl. acc. | p = 0.01 | p = 0.01 |  |  | p = 0.03 | p = 0.004 |
| Right nucl. acc. | p = 0.01 | p = 0.04 |  |  | p = 0.01 | p = 0.02 |
| Left caud. nuc. | p = 0.01 | p = 0.03 | p = 0.03 |  | p = 0.01 | p = 0.003 |
| Right caud. nuc. | p = 0.02 | p = 0.02 | p = 0.02 |  | p = 0.02 | p = 0.001 |

This shows that the analysis of MR images performed 72 hours after a stroke by the method of the invention allows identifying patients likely to develop cognitive disorders 6 months after the onset of stroke.

In this example, the following features: skewness, kurtosis, correlation and entropy, are correlated with the hippocampus volume changes between 72H and M6 exams after a stroke. The Pearson correlation coefficients are 0.52, 0.60, −0.65, −0.67, respectively. ANOVA analyses give the following p-values: p=0.01, p=0.02, p=0.01, p=0.01, respectively, which indicates a strong relevance of the correlation.

Skewness from first-order statistics and entropy from second-order statistics are also correlated with the neuropsychological MoCA score in the considered embodiment. The Pearson correlation coefficients are 0.55, and 0.47, respectively. ANOVA analyses give the following p-values: p=0.01 and p=0.001, respectively, which show that these data exhibit also a significant correlation.

To establish a comparison with the volumetric approach, the evolution of the volume of different structures of interest for MCI and non-MCI patients groups has been examined using a one way analysis of covariance (ANCOVA) with age and gender as covariates. The results show no significant differences in the volumes of any of the considered structures of interest 72 hours after a stroke between MCI and non-MCI groups, with a p-value >0.43. This confirms that the beginning of the cognitive decline is not observable 72H post-stroke by this approach. The method of the invention is thus more sensitive than the state-of-the-art volumetric approach.

ANOVA analyses of the extracted features computed from the down-sampled structures reveal similar results as those reported in the above table for the full structures.

In the case where the classifier is a support vector machine, the texture features are preferably extracted for each brain structure and then some features are selected by using a Principal Components Analysis, a z-score normalization being further applied to the selected features. In the considered example, PCA applied on the features of all the anatomical structures has allowed keeping seven relevant features: mean, skewness, kurtosis, entropy, correlation, sum average and fractal dimension.

The output score of the classification is a probability for a patient to be in one of these profiles: with MCI or without MCI.

The accuracy of the invention using a SVM classifier on the full structures was about 97% on the training data. When applied on the testing set, the method produced the right classification for 17 patients, that is to say for 85% of the set. For the method performed on the down-sampled structures, classification rate on testing data was about 75%.

In another embodiment, the classifier is a classification and regression tree. The table below summarizes the results, in term of Area Under the Receiver Operating Characteristic curve (AUROC), of this example of classification according to the invention computed for different brain structures for the training and testing data.

|  | AUROC (Training data) | | | AUROC (Testing data) | | |
| --- | --- | --- | --- | --- | --- | --- |
| Structure | Global | Left | Right | Global | Left | Right |
| Hippocampus | 0.85 | 0.90 | 0.92 | 0.80 | 0.79 | 0.81 |
| Entorhinal Cortex | 0.84 | 0.89 | 0.90 | 0.82 | 0.80 | 0.83 |
| Pallidum | 0.83 | 0.77 | 0.87 | 0.70 | 0.71 | 0.70 |

|  | AUROC (Training data) | | | AUROC (Testing data) | | |
|---|---|---|---|---|---|---|
| Structure | Global | Left | Right | Global | Left | Right |
| Putamen | 0.91 | 0.93 | 0.95 | 0.73 | 0.75 | 0.74 |
| Nucleus accumbens | 0.80 | 0.90 | 0.86 | 0.77 | 0.79 | 0.77 |
| Caudate nucleus | 0.88 | 0.90 | 0.86 | 0.70 | 0.70 | 0.69 |
| Amygdala | 0.91 | 0.95 | 0.91 | 0.68 | 0.65 | 0.70 |
| Thalamus | 0.90 | 0.86 | 0.95 | 0.78 | 0.77 | 0.79 |

These results show that the method according to the invention is reliable and very efficient for predicting risks of neurodegenerative decline.

Example 2: Second Example for Post-Stroke Cognitive Impairment

In this example, one hundred and sixty consecutive patients from the STROKDEM cohort are used. Cognitive status is assessed by MoCA scores. Cognitive impairment is defined by a score <26, which is a validated cut-off in stroke patients. To control for educational status, one point is added to the MoCA score in patients with less than 12 years of education. For the cognitive outcome, an extensive battery of neuropsychological tests, broadly classified into four cognitive domains (executive function/attention, memory, language, visuospatial ability) is performed on patients at each follow-up time point. For every patient, a test-specific z-score is calculated based on available norms corrected for age, sex, and education. A summary domain-specific z-score is obtained by averaging the test-specific z-scores in each domain. A summary z-score≤1.5 in at least one domain is used to determine cognitive impairment. Finally, cognitive impairment is defined as a global score ≥0.5.

The previously-acquired brain images are also acquired from 3DT1W MR images with 1 mm³ voxel size acquired on 3-T MR machines. This example focuses on patients 72 h post-stroke, thus on 72H images.

The patients are divided into two groups as a function of their cognitive status six months after stroke, thanks to the above-described cognitive assessment. Thus, seventy-five patients are diagnosed with impairment in one or more cognitive domains, while the remaining eighty-five patients are considered cognitively healthy. The table below summarizes the demographic and clinical data of the tested patients.

In a recent study using the same cohort, the deformation of the hippocampus and the atrophy of the entorhinal cortex are identified as anatomical signatures of long-term cognitive impairment in stroke patients. This example thus focuses on these two structures. Left and right structures of each hemisphere were extracted from the T1W images using the FreeSurfer software package using the cross-sectional pipeline with default parameters and intensities normalization. Results are checked visually and corrected if appropriate. The volumes are then computed from the raw FreeSurfer segmentations as the sum of the bilateral volumes. Normalization was done by dividing the result by the intracranial volume (ICV).

To evaluate the differences between the two groups of patients, the first and second order texture features of the considered brain structures are compared using ANCOVA with age and gender as covariates. In the case of significant differences between the two groups, a post hoc t-test is performed. The ICV normalized volumes of left and right parts of the hippocampus as well as of the entorhinal cortex are compared between the two groups of patients using the Mann-Whitney test. The relationships between the hippocampus and entorhinal cortex texture features at 72H with the M6 MoCA and MMSE scores are examined using Spearman correlation. Significance is fixed to a p-value less than 0.05.

In this example, the classifier is a support vector machine with Gaussian kernel. Gaussian kernel was used. The model is build using the texture features that have exhibited significant differences between the two groups of patients, patient's age and sex. As the texture features have different value ranges, a z-score normalization of the features is applied beforehand, as a pretreatment.

SVM is a supervised algorithm that requires a learning step to optimize the model parameters. As the quality of the learned model can be impacted by the learning data, in this example, a k-fold cross-validation scheme is used for the validation. The data set is randomly split into k folds, where k−1 folds are used to train the model and the kth fold is the testing set. For the considered embodiment, k is set to 5. The global validation approach consists in repeating the 5-fold validation 5 times, and the global classification accuracy is expressed as the mean±SD.

Figure 2:
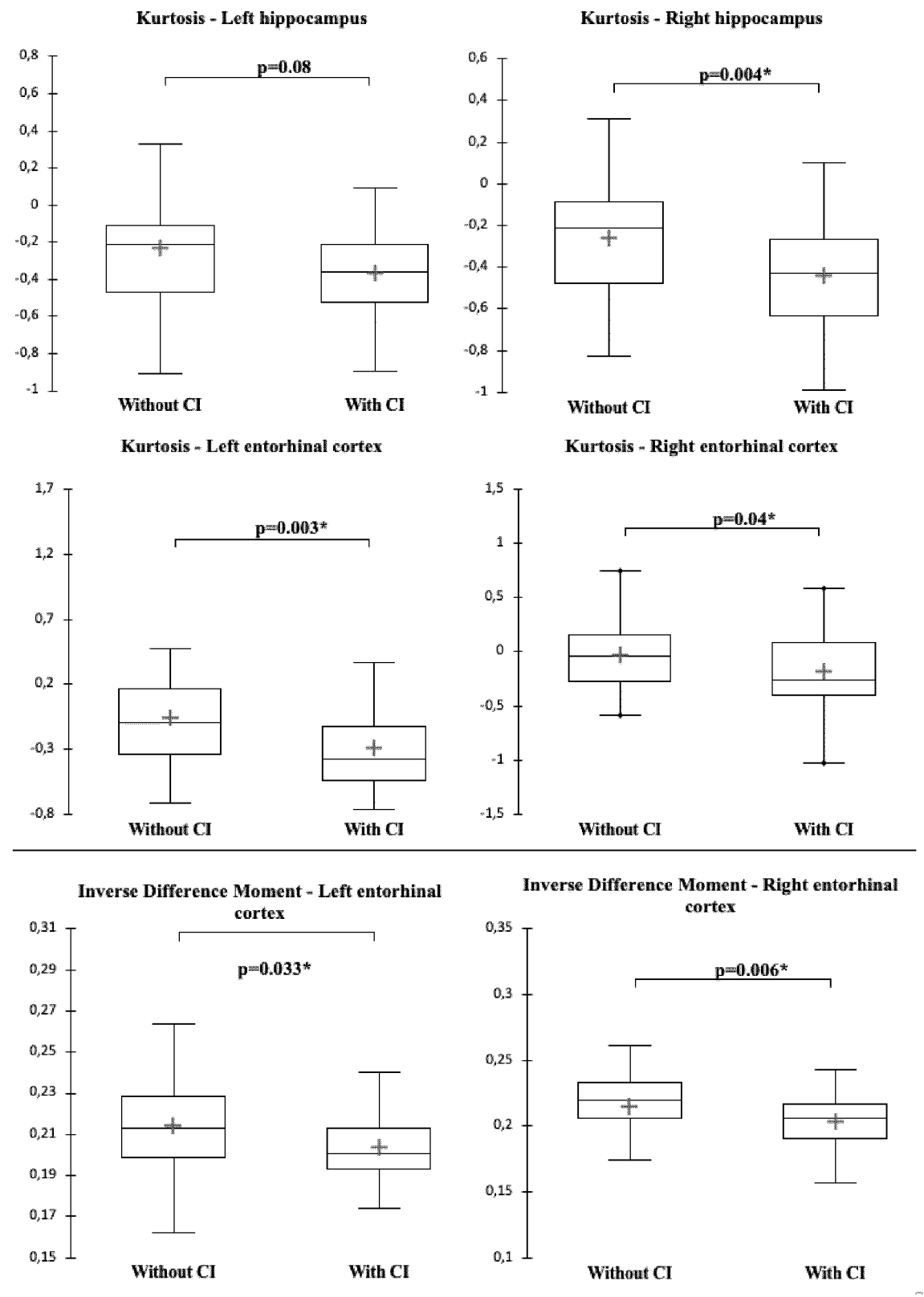
FIG. 2 shows results for an embodiment of the invention concerning post-stroke cognitive impairment.

For the hippocampus, only the kurtosis is significant for the right part, while for the entorhinal cortex, kurtosis is significant for both parts. For the second order statistics, inverse difference moment is significant for both side of the entorhinal cortex. The table below groups the results for all the texture features, and FIG. 2 depicts the main results (the unit of the vertical axis is arbitrary of signal intensity).

The two structures volumes measurements, using region of interest-based methods (ROI), indicates no significant group effect, as can be seen on the table below.

Figure 3:
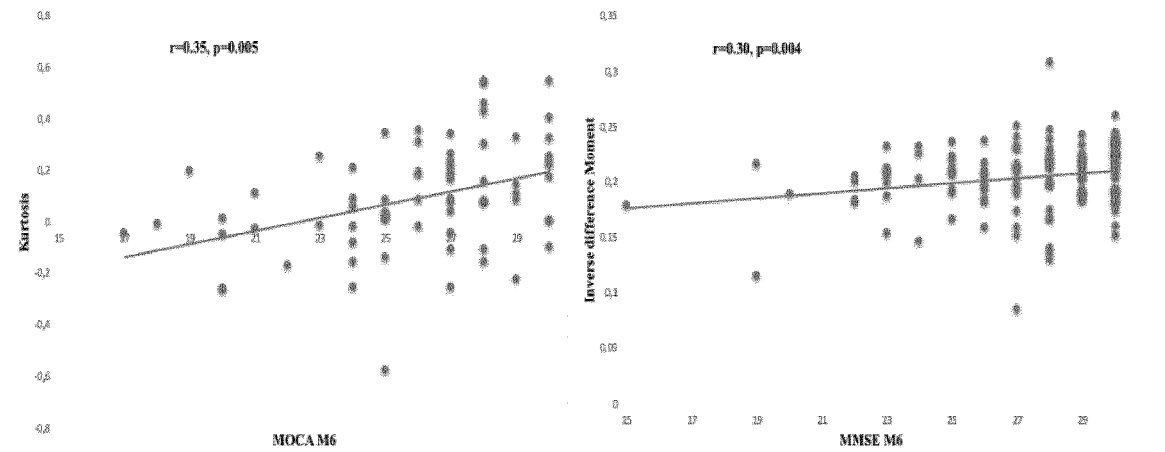
FIG. 3 shows dots plots of texture features distribution versus cognition scores in the embodiment of FIG. 2.

Correlation analysis of texture features and cognitive scores at M6 exhibits significant interactions. The kurtosis measured in the hippocampus is significantly correlated with the MoCa (right part, r=0.35, p=0.005, and left part, r=0.28, p=0.023 respectively). This feature exhibits also significant correlations when measured in the entorhinal cortex: with the MoCa, right part, r=0.28, p=0.044, and left part, r=0.26, p=0.012 respectively. For the same brain structure, inverse difference moment exhibits significant correlations with the MoCa (right part, r=0.22, p=0.024, and left part, r=0.23, p=0.03 respectively) and the MMSE (right part, r=0.30, p=0.004, and left part, r=0.2, p=0.02 respectively). FIG. 3 depicts dots plots of texture features distribution versus cognition scores (left plot: Kurtosis from the right hippocampus versus MoCA score, right plot: inverse difference moment in the right entorhinal cortex versus the MMSE score).

The SVM model is trained by considering the kurtosis measured in both parts of the two considered brain structures, the inverse difference moment computed in the entorhinal cortex, and patient age and sex. The 5-fold validation process shows an accuracy of 88±3% of correct prediction of CI occurrences.

Example 3: Quantification of Post-Ischemic Neuronal Loss in a Stroke Model

In this example, Wistar rats weighing 280 to 320 g are randomized 1:1 to sham or ischemia-reperfusion (IR) groups. It has to be noted that all the experiments are done in accordance with the institutional and national guidelines for the care and use of laboratory animals and were approved by the local animal care and use committee (Comité d'Ethique en Experimentation Animale du Nord-Pas de-Calais, Lille, France; reference: 00455.02).

For the IR group, after cerebral ischemia induction by transient middle cerebral occlusion; the animals are randomized again into four groups corresponding to four examination times: 24 hours post ischemic procedure (24H), one week (D7), 1 month (M1) and 2 months (M2). At each experimentation time, magnetic resonance images are acquired on the animals, which are then sacrificed, and histology analysis is realized.

Amongst the different existing ischemic stroke models, in this example, the middle cerebral artery occlusion model is used, which models focal infarction in a large vascular territory and does not require craniotomy. After anaesthesia, the ostium of the right middle cerebral artery was occluded with an intraluminal monofilament. Reperfusion was initiated after 1 hour by removing the monofilament. Animals in the sham group underwent a similar surgical procedure, without introduction of the monofilament. Both sham and IR groups underwent magnetic resonance imaging using a 7 testla, 20 cm bore superconducting magnet (BioSpec®, Bruker, Ettlingen, Germany). Morphologic images using a T2-Weighted (T2w) sequence were acquired with the following parameters: spin-echo, 20 slices with a thickness of 0.75 mm in the axial plane, matrix size=256×256 pixels, TR=3000 ms, TE=33 ms, and pixel size=0.156×0.156 $mm^2$.

Images were first treated for inhomogeneity correction using the nonparametric non-uniform intensity normalization algorithm (N3), and then texture features are extracted on a ROI defining the hippocampus. This ROI is automatically segmented by aligning the image on a well-known labelled atlas of the rat brain. An affine registration transformation with twelve parameters was used in the alignment to overcome differences in brain volume between the atlas and the used animals.

In this example, texture features include first order statistics and second order statistics. First order features are mean and standard-deviation of grey levels in the ROI, skewness and kurtosis. Second order statistics are derived from grey level co-occurrence matrices, built using 26-connected directions of neighbouring voxels in 3D space and a distance D set to 1 voxel. Seven features were then computed: homogeneity, contrast, entropy, correlation, variance, sum-average, and inertia.

Figure 4:
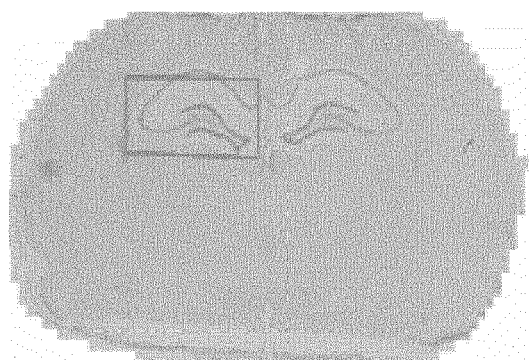
FIG. 4 represents a visual spatial registration between MR images and histology for an embodiment of the invention concerning the quantification of post-ischemic neuronal loss in a stroke model.
Figure 4:
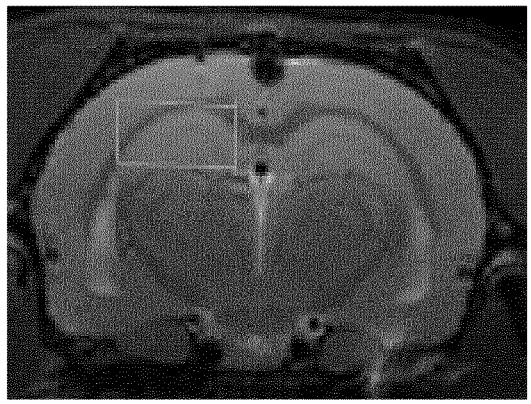
Figure 6:
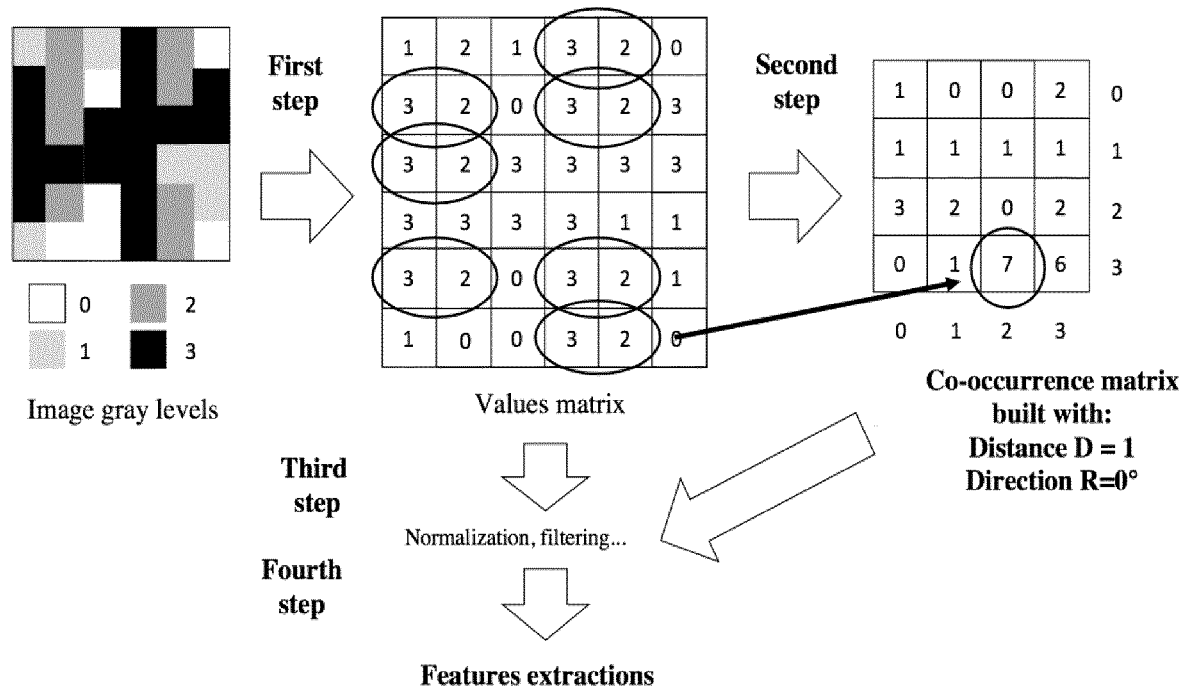
FIG. 6 illustrates an example of the building of a grey levels co-occurrence matrix.

In this example, the comparison of neural cell densities between the two sham and IR groups is performed using a non-parametric Mann-Whitney test. For the analysis of the association between texture features and neural cell densities, first a visual spatial registration, visible at FIG. 4, is performed to define correspondences between the MR images and histological slices. Then Spearman's correlation is used to study correlations between MR texture features and neural densities. In case of significant correlation of a parameter, a non-parametric Mann-Whitney test is performed to compare the distribution between the two groups, the threshold of significance being set to $p<0.05$.

A total of 57 rats were used for the considered example: 13 in the 24H group with 9 in the IR group and 4 sham, 18 in the D7 group with 6 IR and 12 sham, 15 in the M1 group with 6 IR and 9 sham and lastly 11 in the M2 group with 9 IR and 2 sham.

For the four considered experiments times, a reduction in the neural cells density in the IR groups is observed:
  H24: 2541.42±217.70 in IR group and 3382.33±946.27 in sham group,
  D7: 2223.2±331.83 in IR group and 7580.6±1303.59 in sham group (p=0.001),
  M1: 2364.2±398.48 in IR group and 5310±1057.33 in sham group (p=0.05), and
  M2: 2589.12±408.34 in IR group and 5232±281 in sham group.

Spearman correlation analyses between the texture features and neural cells densities in the histological slices reveal significant interactions for four features, mean, skewness, correlation and sum-average, for the four considered experiments times. Mean and skewness are negatively correlated with cell density, whereas correlation and sum-average correlate positively with cell density (see the table of FIG. 5). Post-hoc comparison of these features between the IR and sham groups indicates significant differences.

Example 4: Cognitive Deficits Due to Parkinson's Disease

The invention can be also applied on Parkinson's disease (PD).

In a fourth example, data coming from a previous study involving two independent centres in Lille, France and Maastricht, The Netherlands, are used. All patients gave informed consent prior to participation in the study which was in accordance with the Declaration of Helsinki and was approved by the local institutional review boards (ClinicalTrials.gov Identifier: NCT01792843).

All patients met the United Kingdom Brain Bank diagnostic criteria for PD. Are excluded patients with moderate and severe dementia, defined as a score superior to 1 on the Clinical Dementia Rating scale, and meeting the Movement Disorders criteria for PD, patients older than 80 years, patients with neurodegenerative disorders other than PD, patients treated with deep brain stimulation or those meeting contra-indications for MRI. All patients received stable doses of antiparkinsonian medication and were tested in their "on drug" state.

The patients underwent a neurological examination and an extensive neuropsychological test battery. The Movement Disorder Society-Unified Parkinson's disease Rating Scale (MDS-UPDRS, sections I-IV) was used to measure severity and experiences of non-motor and motor symptoms, and the Hoehn and Yahr staging scale to measure disease stage. Severity of depression, anxiety and apathy was respectively assessed by the score at the 17-item Hamilton Depression Rating Scale (HAMD), the Parkinson Anxiety Scale (PAS) and the Lille Apathy Rating Scale (LARS). The Mattis dementia rating scale (Mattis DRS) was used to assess global cognition. Attention and working memory were assessed with the forward and backward digit span and the Symbol Digit Modalities Test (SDMT). Executive functioning was measured with the Trail Making Test (TMT, B/A ratio), the interference index of the Stroop word color test, and the word generation task, i.e. with single and alternating phonemic conditions.

MRI images were acquired on a 3T whole-body scanners (Achieva TX, Philips Healthcare, Best, the Netherlands) using an eight-channel SENSE head coil. High-resolution 3D T1weighted images were acquired in the sagittal plane with 256×256 matrix and 1 $mm^3$ isotropic voxel size.

A total of 102 (Lille, n=52 and Maastricht, n=50) patients were included and they were classified by a non-supervised cluster analysis into three different clusters according to their cognitive status: cognitively intact patients (PDCN), cognitively intact patients with slight mental slowing (PDCN-S) and patients showing mild cognitive deficits, particularly in executive functioning (PD-EXE).

The demographic and clinical characteristics of the patient groups are described in the below table.

| Total (n = 102) | PDCN (n = 30) | PDCN-S (n = 29) | PD-EXE (n = 43) | p-value |
|---|---|---|---|---|
| Age (y) | 60.18 ± 8.51 | 65.23 ± 5.11 | 66.65 ± 7.91 | 0.001 |
| Sex (F/M) | 10/20 | 9/20 | 16/27 | — |
| Education | 13.26 ± 3.4 | 13.41 ± 4.17 | 11.63 ± 3.59 | 0.053 |
| Disease duration (y) | 7.7 ± 5.20 | 8.69 ± 7.87 | 8.81 ± 5.02 | 0.46 |
| Hoehn & Yahr stage | 1.92 ± 0.39 | 2.19 ± 0.54 | 2.21 ± 0.59 | 0.033 |
| MDS_UPDRS3 score | 26.02 ± 11.70 | 29.31 ± 12.39 | 28.74 ± 11.44 | 0.38 |
| Mattis DRS (Score on 144) | 140.95 ± 3.01 | 140.24 ± 2.85 | 134.30 ± 5.39 | <0.0001 |
| SDMT (N, refering to the number of items correctly coded in 90 seconds) | 55.37 ± 8.25 | 43.64 ± 3.5 | 32.87 ± 6.48 | <0.0001 |

Changes in the following structures are investigated: the thalamus, the hippocampus, the putamen, the *pallidum*, the caudate nucleus and the amygdala.

After segmentation and intensity normalization using the automatic Freesurfer pipeline, with visual checking and manual correction if appropriate, texture features are extracted for each structure by considering left and right parts as ROI. In this example, four features from the first order statistics and seven second order statistics features are estimated in each ROI. First order statistics are: mean and standard-deviation of grey levels in the ROI, skewness and kurtosis.

Second order statistics are derived from the grey level co-occurrence matrix, shown in FIG. 5. The matrix is built with neighbouring set to 1 voxel and direction 0°. For example, the grey level 3 is directly followed, i.e. distance D=1 voxel, by grey level 2 at the right 7 times, the grey level 2 is directly followed by the grey level 1 at the right side twice, etc.

In the present example, co-occurrence matrices were built using 26-connected directions of neighbouring voxels in 3D space and a distance D set to 1 voxel. Seven features were then computed: homogeneity, contrast, entropy, correlation, variance, sum-average, and inertia.

Since brain atrophy was reported in PD's patients with CI, brain volume variations were investigated among the three considered groups of patients. Two classical methods were explored, the method based on ROIs volume measurements and the voxel-based morphometry (VBM). For the first, bilateral parts of each selected brain structure were measured and normalized to the total intracranial volume (TIV) using two different approaches, the ratio-approach where the corrected volume is measured as the ratio of the regional brain region to the TIV and the residual method where the volume is corrected by estimating the linear regression between the volumes and the TIVs in all the subjects.

As the texture features computed as described above are correlated by principle, a features selection strategy was first applied to select the most associated with the groups distribution. A Spearman's rank correlation with a significance fixed to p<0.01 instead of the traditionally value of 0.05 was used to study this association, in order to keep only the most important features. The selected features were injected separately in a multivariate regression analysis with patient age as co-variable to test confounding effect due to differences between groups, visible at the table above.

Secondly, for the selected features, the Kruskall-Wallis test with Bonferroni correction for multiple tests was used for inter-group comparison and Dunn's tests for pair-wise comparisons. Lastly, association between the selected texture features and cognition was examined by measuring the Spearman correlation with the scores at the MDRS and the SDMT. The latter is of particular interest because it is known to be discriminant and to allow detecting a specific cluster of patients according to their cognitive profiles. Hence, if some texture features correlate with performance at the SDMT, they could represent potential biomarkers of mental slowing in PD.

For the volumes and for the ROIs based approach, comparisons of the variations within the three groups were done using the Kruskall-Wallis test (significance fixed to p<0.05). For the VBM method, t-tests were performed to identify differences in whole brain grey matter volume between the patient groups. Clusters were considered significant using the family-wise error (FWE) threshold of $p_{FWE}$<0.05.

The texture features revealed as significant in differentiating the three cognitive profiles were used to build a classification model using a non-linear learning algorithm, as previously described. In this example, Support Vector Machines were used. The data set was partitioned into 5 sub-sets and 5 rotational training-evaluations were done, by considering at each time 4 subsets for the training and the remaining set for the validation.

Detailed Spearman correlation results are shown in the table below. The used features selection strategy allows highlighting two features as the most correlated features with the distribution of the groups: skewness and entropy, especially for the hippocampus (left and right parts). Entropy is also significant for the thalamus for both hemispheres while skewness is only significant for left thalamus. Entropy is also significant for the left and right amygdala.

| | Skewness Spearman correlation coefficient | p-value | Entropy Spearman correlation coefficient | p-value |
|---|---|---|---|---|
| Hippocampus R | −0.42 | <0.0001 | −0.33 | 0.001 |
| Hippocampus L | −0.30 | 0.008 | −0.35 | <0.0001 |
| Amygdala R | −0.10 | 0.25 | −0.24 | 0.01 |
| Amygdala L | −0.15 | 0.13 | −0.21 | 0.01 |
| Thalamus R | −0.05 | 0.4 | −0.265 | 0.01 |
| Thalamus L | −0.3 | 0.003 | −0.34 | <0.0001 |
| Pallidum R | −0.15 | 0.12 | −0.14 | 0.14 |
| Pallidum L | −0.16 | 0.11 | −0.12 | 0.20 |
| Putamen R | −0.07 | 0.44 | 0.10 | 0.27 |
| Putamen L | −0.22 | 0.02 | −0.13 | 0.07 |
| Caudate Nucleus R | −0.10 | 0.3 | −0.167 | 0.09 |
| Caudate Nucleus L | 0.21 | 0.02 | −0.25 | 0.011 |

As shown in a further table below summarizing results of multinomial multiple regression analyses of the association between the two texture features 'skewness' and 'entropy' with the patient's groups distribution, with age as covariate, multiple regression analyses confirms that interactions between texture features, reported above, and cognitive profile distribution are significant, independently of age, except for the entropy for the left amygdala and the right thalamus and for the skewness for the left thalamus.

|  | Skewness Wald Test Khi2 (Global) | p-value | Entropy Wald Test Khi$^2$ (Global) | p-value |
|---|---|---|---|---|
| Hippocampus R | 7.78 (18.53) | 0.02 | 6.72 (16.53) | 0.04 |
| Hippocampus L | 6.80 (15.37) | 0.05 | 7.12 (16.39) | 0.03 |
| Amygdala R | — | — | 6.20 (15.30) | 0.05 |
| Amygdala L | — | — | 2.82 (14.73) | 0.2 |
| Thalamus R | — | — | 3.05 (14.74) | 0.2 |
| Thalamus L | 0.28 (12.78) | 0.86 | 6.23 (15.72) | 0.04 |

Figure 7:
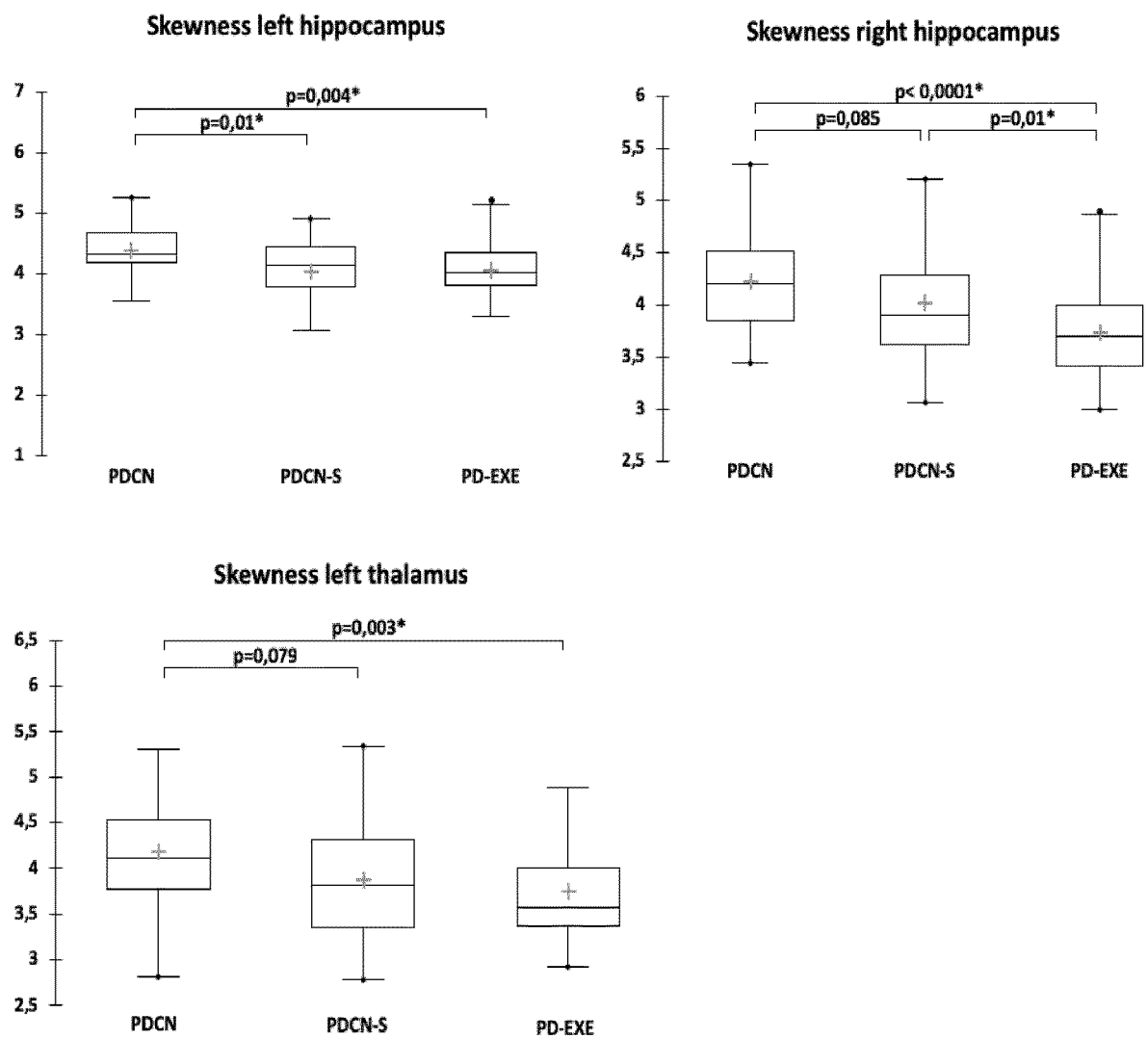
FIG. 7 represents plot boxes with Dunn's test results for pairwise comparisons of the texture feature skewness extracted according to the invention and used for the assessment of Parkinson's disease.
Figure 8:
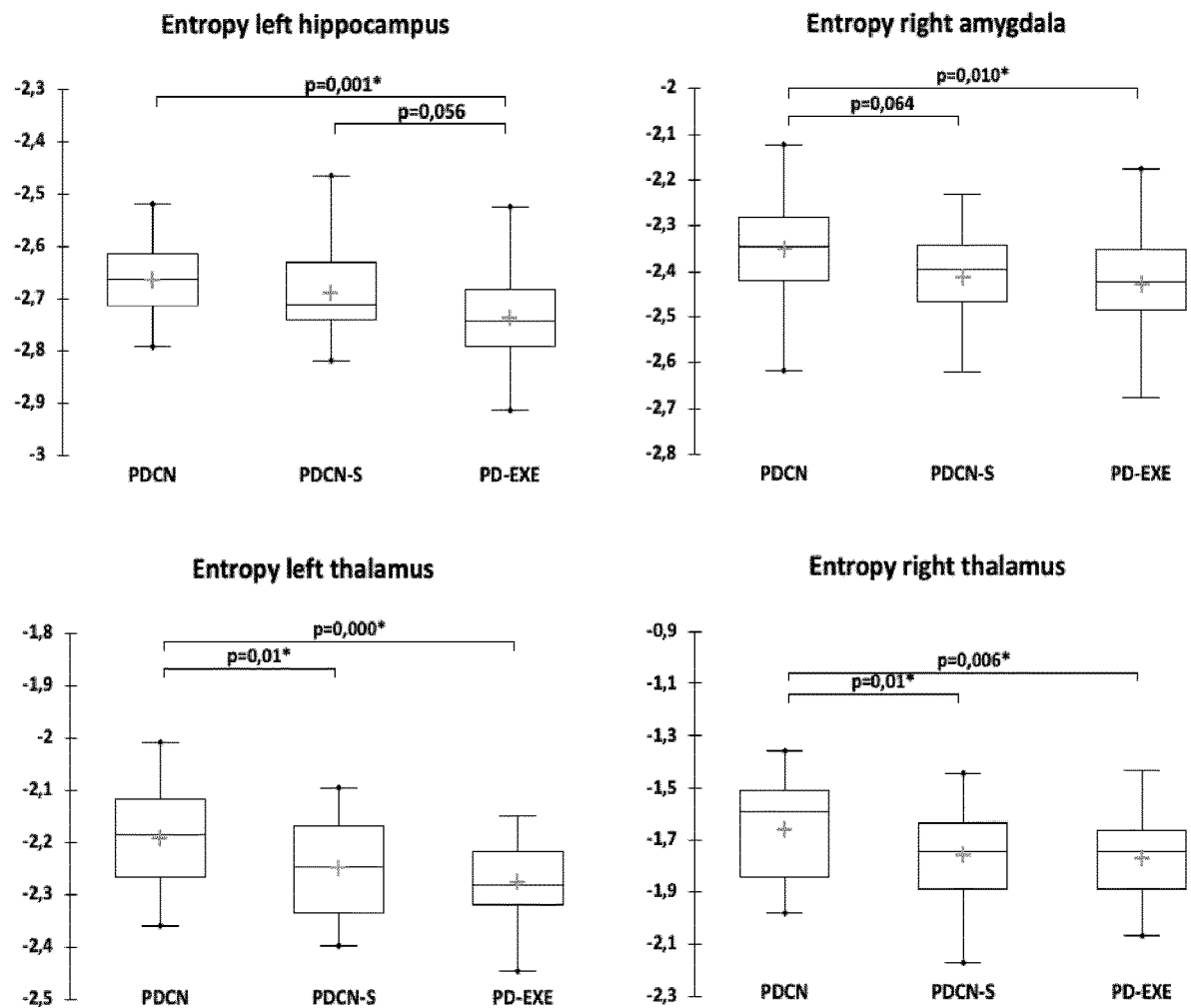
FIG. 8 represents plot boxes with Dunn's test results for pairwise comparisons of the texture feature entropy extracted according to the invention and used for the assessment of Parkinson's disease.

In-between group comparisons, whose results are summarized in FIGS. 7 and 8, reveal that the use of skewness extracted from the hippocampus is able to discriminate the three groups by significant differences between PDCN versus PDCN-S, PDCN versus PD-EXE and PDCN-S versus PD-EXE, while entropy measured in the three brain structures was mainly able to discriminate PDCN from PD-EXE and PDCN from PDCN-S. FIG. 7 represents plot boxes with Dunn's test results for pairwise comparisons of the texture feature skewness (Bonferroni corrected p-value=0.0167), while FIG. 8 represents plot boxes with Dunn's test results for pairwise comparisons of the texture feature entropy (Bonferroni corrected p-value=0.0167).

When correlating the selected texture features 'skewness' and 'entropy' with cognition scores, the results show that both features measured in the hippocampus and the thalamus are significantly correlated with performance at the symbol digit modalities and Mattis Dementia Rating Scale test, while only entropy measured from the amygdala is significantly correlated to these two scores, as shown in the table below, summarizing Spearman correlation study results for both the texture features with said two scores.

|  |  | Symbol Digit Modalities Test scores (SDMT) | | Mattis Dementia Rating Scale (MDRS) | |
|---|---|---|---|---|---|
|  | Features | r | p-value | r | p-value |
| Hippocampus R | Skewness | 0.36 | 0.001 | 0.23 | 0.042 |
|  | Entropy | 0.25 | 0.026 | 0.15 | 0.17 |
| Hippocampus L | Skewness | 0.25 | 0.031 | 0.28 | 0.01 |
|  | Entropy | 0.33 | 0.003 | 0.12 | 0.18 |
| Amygdala R | Skewness | 0.10 | 0.52 | 0.11 | 0.33 |
|  | Entropy | 0.30 | 0.007 | 0.27 | 0.014 |
| Amygdala L | Skewness | 0.09 | 0.73 | 0.02 | 0.88 |
|  | Entropy | 0.12 | 0.25 | 0.31 | 0.002 |
| Thalamus R | Skewness | 0.13 | 0.20 | 0.17 | 0.13 |
|  | Entropy | 0.31 | 0.005 | 0.06 | 0.54 |
| Thalamus L | Skewness | 0.27 | 0.017 | 0.29 | 0.01 |
|  | Entropy | 0.32 | 0.003 | 0.14 | 0.20 |

Brain structures volumes measurements, using ROIs based methods, indicate no significant group effect. Detailed measures and statistical comparisons are shown in the table below, summarizing results of Kruskall-Wallis tests for the groups comparison after TIV normalization using the ratio and residue methods (volumes expressed in millilitres-mL).

|  | PDCN | PDCN-S | PD-EXE | Ratio normalization p-value | Residual normalization p-value |
|---|---|---|---|---|---|
| TIV | 1174.02 ± 103.73 | 1165.01 ± 120.14 | 1117.20 ± 120.77 |  |  |
| Hippo. R | 4.56 ± 0.48 | 4.28 ± 0.55 | 4.02 ± 0.49 | 0.17 | 0.09 |
| Hippo. L | 4.48 ± 0.48 | 4.32 ± 0.54 | 4.02 ± 0.52 | 0.44 | 0.1 |
| Amygdala R | 1.75 ± 0.22 | 1.64 ± 0.26 | 1.54 ± 0.23 | 0.09 | 0.09 |
| Amygdala L | 1.66 ± 0.24 | 1.57 ± 0.27 | 1.43 ± 0.23 | 0.08 | 0.1 |
| Thalamus R | 7.33 ± 0.81 | 7.15 ± 0.84 | 6.76 ± 0.67 | 0.95 | 0.08 |
| Thalamus L | 8.18 ± 1.00 | 7.96 ± 0.98 | 7.44 ± 0.76 | 0.96 | 0.09 |
| Pallidum R | 1.54 ± 0.21 | 1.55 ± 0.23 | 1.54 ± 0.16 | 0.37 | 0.55 |
| Pallidum L | 1.54 ± 0.20 | 1.55 ± .025 | 1.53 ± 0.22 | 0.7 | 0.52 |
| Putamen R | 5.01 ± 0.69 | 4.92 ± 0.70 | 4.84 ± 0.53 | 0.61 | 0.25 |
| Putamen L | 5.15 ± 0.72 | 4.92 ± 0.64 | 4.81 ± 0.57 | 0.70 | 0.31 |
| CN R | 3.90 ± 0.63 | 3.78 ± 0.78 | 3.75 ± 0.66 | 0.68 | 0.23 |
| CN L | 3.77 ± 0.61 | 3.68 ± 0.60 | 3.55 ± 0.608 | 0.18 | 0.14 |

For the VBM method, none of the pair-wise comparisons PDCN vs. PDCN-S, PDCN-S vs. PD-EXE and PDCN-S vs. PD-EXE highlights regions with significant differences. Skewness and entropy from the hippocampus, thalamus and amygdala are thus selected to train the SVM model. The cross-validation process shows an accuracy of about 86±4% of correct groups classification.

Example 5: Nigrostriatal Pathway Correlation with PD Symptoms

As neurodegenerative pathology, PD is characterized by a predominant and progressive loss of dopaminergic neurons in the nigrostriatal pathway. Patients fulfil the clinical criteria for PD when approximately 60-70% of the neurons in the substantia nigra (SN) are degenerated and 80% of the striatal dopamine content is reduced. The disease is primarily regarded as a motor syndrome inducing signs as rigidity, akinesia and postural instability, but it induces also numerous and heterogeneous non-motor or neuropsychiatric symptoms involving abnormalities in cognition, speech and behavior.

In a fifth example, in order to test texture features variation sensibility in regard with the disease severity, two different populations of PD patients are considered, mainly differing in term of disease duration. For both populations, the clinical diagnosis criterion is the one of the Movement Disorders Society (MDS). Patients with severe cognitive impairment or dementia (MoCA score <24 and DSM-IV criteria), patients with psychiatric disorders (psychosis, hallucinations, compulsive disorders, substance addiction, bipolar disorder, severe depression, . . . ), as assessed in a semi-structured interview with a psychiatrist, according to the Diagnostic and Statistical Manual of Mental Disorders, Fourth Edition, Text Revision, 2000, patients with severe brain atrophy or abnormal MRI for any other reason than PD are excluded from the study.

This study was approved by the local independent ethics committee (CPP Nord Ouest IV, Lille, France). All patients provided their written, informed consent to participation. The study strictly followed the methods, the guidelines and the regulations described in the approved protocol (i.e. an ancillary study to the PREDISTIM study (ClinicalTrials.gov identifier: NCT02360683).

For the first population, "PD cohort 1", patients are prospectively enrolled by 19 movement disorders departments throughout France, and have a mean disease duration of 8.6 years (STD=4.1 years, min=1 year and max=30 years). A total of 327 consecutive patients is considered. They all underwent a complete clinical assessment in the worst-off and in best-on conditions. For the second population, "PD cohort 2", patients are enrolled from a unique center in Lille, France, and have a mean disease duration of 0.45 years (STD=0.46 years, max=2.43 years). A control group of 32 subjects matched to the patients with PD for age and sex is also included. None of these subjects had a history of head injury, neurological or psychiatric diseases. The demographic and clinical data of the three groups are reported in the table below.

|  | PD cohort 1 | PD cohort 2 | Controls | p |
|---|---|---|---|---|
| n | 327 | 39 | 32 | |
| Sex (M/F) | 209/118 | 22/17 | 18/14 | 0.38 (Pearson chi-square test) |
| Age (years) | 59.5 ± 8.7 | 63 ± 10.4 | 61.6 ± 10.8 | 0.42 (Kruskall-Wallis test) |
| Disease duration (years) | 8.6 ± 4.1 | 0.45 ± 0.46 | — | |
| MDS-UPDRS_1 | 10.9 ± 5.7 | 8.25 ± 5.70 | — | |
| MDS-UPDRS_4 | 8.1 ± 3.9 | — | — | |
| Hoehn_Yahr score (ON) | 1.21 ± 0.85 | 1.80 ± 0.57 | — | |
| Hoehn_Yahr score (OFF) | 2.61 ± 0.89 | — | — | |
| Schwab_England (ON) | 9.3 ± 1.06 | — | — | |
| Schwab_England (OFF) | 6.82 ± 1.85 | — | — | |
| Dopamine sensibility | 75.8 ± 13.5 | — | — | |
| MDS-UPDRS_3 Best ON | 10.31 ± 7.21 | — | — | |
| MDS-UPDRS_3 Worst OFF | 42.10 ± 15.86 | — | — | |

All patients and subjects brains were scanned on 3T MRI systems. High-resolution 3D T1w images were acquired in the sagittal plane with 256×256 matrix and 1 mm3 isotropic voxel size. The images were processed with the freely available FreeSurfer software package (version 6.0) using the cross sectional pipeline with default parameters. The images were bias field and inhomogeneities were corrected using the N3 algorithm.

The following deep grey matter structures were considered: substantia nigra (SN), nucleus subthalamic nucleus (STN), putamen, *pallidum* and caudate nucleus (CN). For these later regions, left and right parts of each hemisphere were extracted from the images. Results were checked visually and corrected if appropriate. SN and STN were segmented using a software which implements an atlas-based approach. The volume of each structure was estimated from the segmentation, and normalization was done by dividing the result by the intracranial volume (ICV).

For each structure, right and left parts were considered separately and eleven texture features were computed with four from first order statics and seven others derived from second order. First order parameters include: signal intensity mean, standard-deviation, kurtosis, and skewness. The second order features were derived from the gray level co-occurrence matrix with a spatial relationship defined as the relative direction in a given direction d. In this example, the matrix was estimated considering 4 directions 0=0°, 45°, 90° and 135°, and a distance d=1. From this matrix, the following features were computed: homogeneity, contrast, entropy, correlation, variance, sum average and inverse difference moment.

For each brain structure, the normalized volumes were compared between the three groups using a non-parametric Kruskall-Wallis test with significance fixed to $p<0.05$ and Bonferroni correction for multiple tests was applied.

For each structure and for each part of the structure, associations between said ten texture features and the clinical variables MDS_UPDRS_1 (MDS1), MDS-UPDRS_3 Best_ON (MDS3_ON), MDS-UPDRS_3 Worst_OFF (MDS3_OFF), MDS-UPDRS_4 (MDS4), Hoehn&Yahr score ON (HY_ON), Hoehn&Yahr score OFF (HY_OFF), Schwab&England ON (SE_ON), Schwab&England OFF (SE_OFF) and dopamine (Dopa) sensibility were examined in PD cohort 1. Given the number of the features, the clinical variables and the brain structures considered, a features selection strategy was applied to highlight the most significant ones that can be used as predictors. Spearman correlation with a significance fixed to $p<0.05$ was applied. For a given region, only significant correlations in both parts and with a coefficient at least equal to 0.2 in one of the two parts were selected.

For the selected features, multivariate linear regression analyses were performed with incorporation of age, gender and disease duration as co-variables. Lastly, a comparison was performed between the features with significant interactions and those computed in the PD cohort 2 and the control group.

After application of the Bonferroni correction, the corrected p-value was 0.016. None of the five considered brain regions exhibited significant volume differences between PD patients and the ones of the control group, as shown in the table below which summarizes regions of interest-based volumes, expressed in $cm^3$, and results of the Kruskall-Wallis tests for the groups comparison after TIV normalization using the ratio method.

|  | PD cohort 1 | PD cohort 2 | Controls | p-value |
|---|---|---|---|---|
| TIV | 1143.04 ± 142.45 | 1184.51 ± 154.55 | 1193.91 ± 98.50 | |
| SN R | 0.132 ± 0.015 | 0.138 ± 0.02 | 0.144 ± 0.018 | 0.12 |
| SN L | 0.123 ± 0.013 | 0.128 ± 0.016 | 0.142 ± 0.022 | 0.15 |
| STN R | 0.105 ± 0.012 | 0.108 ± 0.019 | 0.112 ± 0.018 | 0.20 |
| STN L | 0.100 ± 0.02 | 0.103 ± 0.017 | 0.106 ± 0.02 | 0.16 |
| Caudate R | 3.79 ± 0.64 | 3.86 ± 0.60 | 3.90 ± 0.50 | 0.22 |
| Caudate L | 3.56 ± 0.60 | 3.65 ± 0.53 | 3.85 ± 0.46 | 0.18 |
| Pallidum R | 1.65 ± 0.32 | 1.86 ± 0.27 | 1.89 ± 0.30 | 0.25 |
| Pallidum L | 1.66 ± 0.37 | 1.89 ± 0.26 | 1.92 ± 0.38 | 0.19 |

-continued

|  | PD cohort 1 | PD cohort 2 | Controls | p-value |
|---|---|---|---|---|
| Putamen R | 4.05 ± 0.75 | 4.50 ± 0.62 | 4.51 ± 0.62 | 0.33 |
| Putamen L | 4.20 ± 0.78 | 4.55 ± 0.58 | 4.57 ± 0.74 | 0.27 |

Figure 9A:
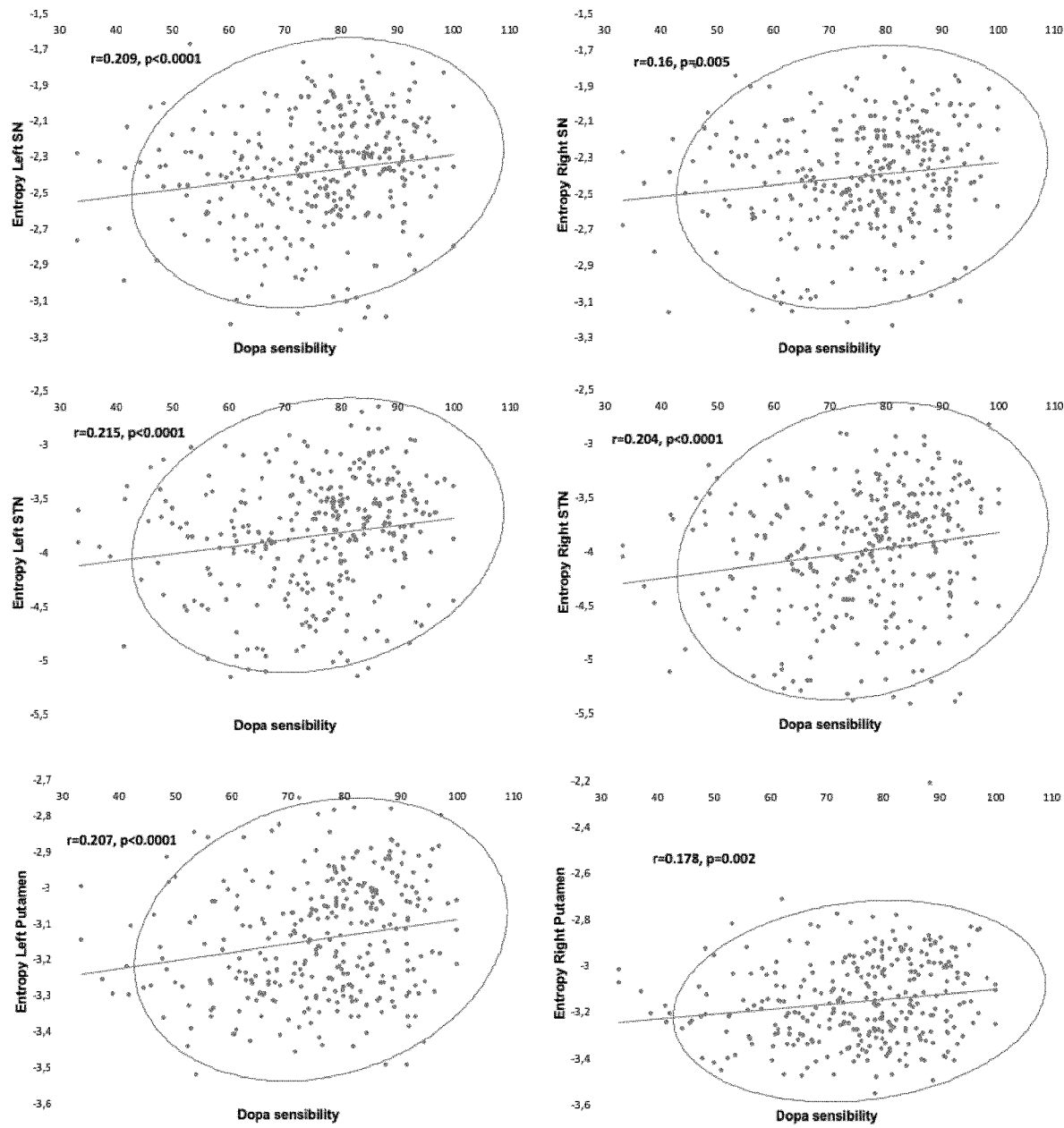
FIGS. 9A and 9B represent dots plots for the distribution of the texture feature entropy versus the sensibility to dopamine in five considered brain structures in a context of nigrostriatal pathway correlation with Parkinson's disease symptoms.
Figure 9B:
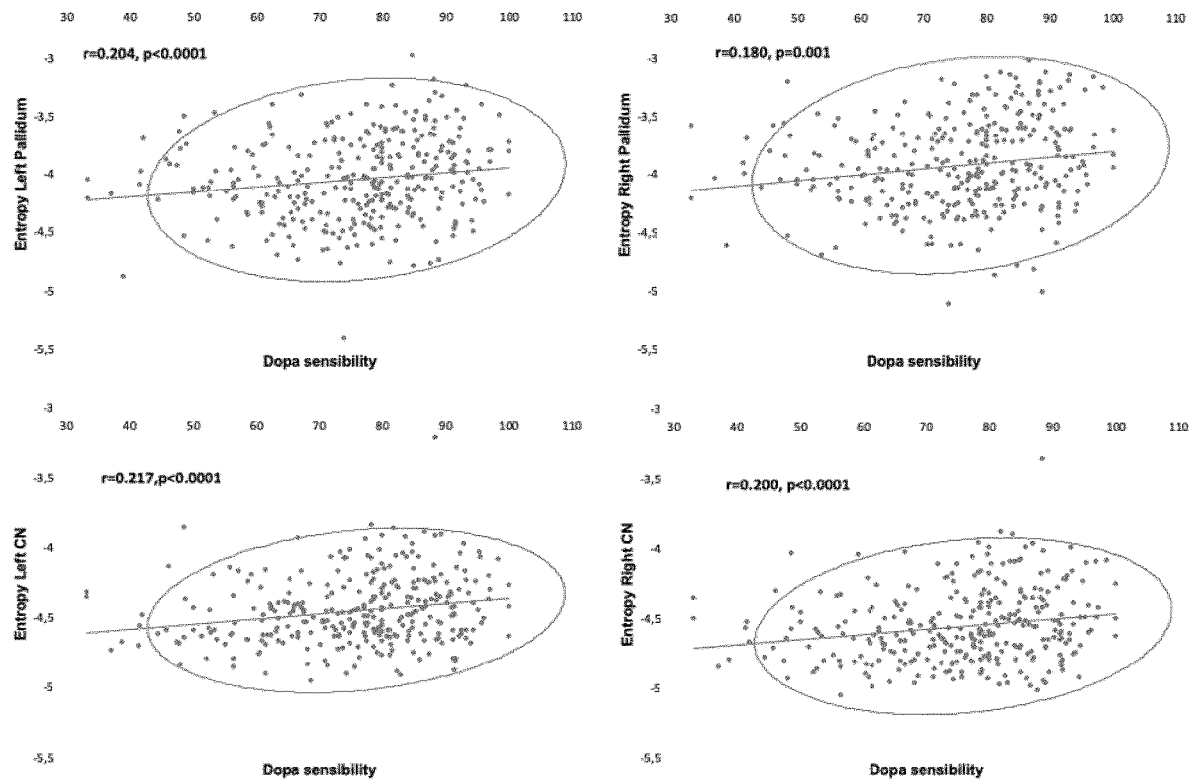

The features selection step allows defining two texture features, entropy and inverse difference moment (IDM), as significantly correlated to some of the clinical variables as the Dopa sensibility, MDS-UPDRS_3 Worst_OFF and Hoehn& Yahr OFF, as summarized in the table below and in FIGS. 9A and 9B, for the five considered brain structures. In the figures, the circles correspond to 95% confidence intervals. The multivariate regressions analyses by incorporating demographic data and disease duration as co-variables confirm the significant interactions between texture features and clinical variables, as reported in the table.

|  | Texture features | Spearman coefficient Left | p-value Left | Spearman coefficient Right | p-value Right |
|---|---|---|---|---|---|
| SN |  |  |  |  |  |
| Dopa sensibility | Entropy | 0.21 | <0.0001 | 0.16 | 0.004 |
| MDS3_OFF | Moy | 0.20 | <0.0001 | 0.19 | <0.0001 |
|  | SD | 0.20 | <0.0001 | 0.17 | <0.0001 |
| STN |  |  |  |  |  |
| HY_ON | SD | 0.20 | <0.0001 | 0.18 | 0.002 |
|  | IDM | −0.21 | <0.0001 | −0.16 | 0.005 |
| Dopa sensibility | Entropy | 0.21 | <0.0001 | 0.20 | <0.0001 |
|  | IDM | 0.21 | <0.0001 | 0.20 | <0.0001 |
|  | Contrast | 0.19 | <0.0001 | 0.20 | <0.0001 |
| Putamen |  |  |  |  |  |
| Dopa sensibility | Entropy | 0.20 | <0.0001 | 0.18 | 0.001 |
| HY_ON | Entropy | −0.21 | <0.0001 | −0.20 | <0.0001 |
| Pallidum |  |  |  |  |  |
| HY_ON | Entropy | −0.16 | 0.006 | −0.21 | <0.0001 |
| Dopa sensibility | Entropy | 0.18 | 0.001 | 0.20 | <0.0001 |
| CN |  |  |  |  |  |
| HY_ON | IDM | −0.18 | 0.001 | −0.21 | <0.0001 |
| Dopa sensibility | Entropy | 0.22 | <0.0001 | 0.20 | <0.0001 |

Figure 10:
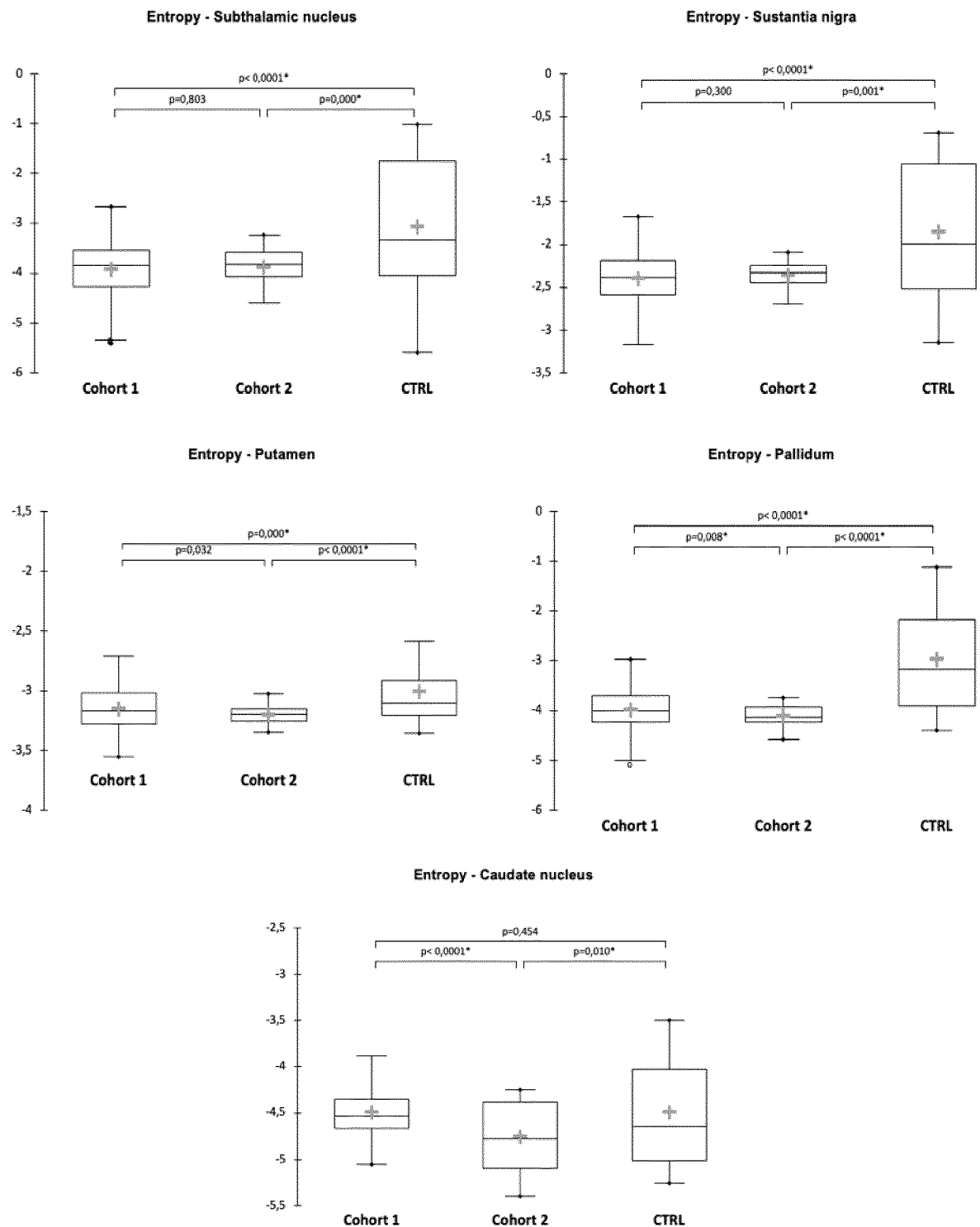
FIG. 10 represents plot boxes representing the entropy distribution in five considered brain regions among two different populations of patients with Parkinson's disease and a control population.

These analyses allow highlighting the texture feature entropy as one of the most correlated features with the clinical data and mainly with dopamine sensibility. The following analysis focuses on this feature and compares it in the two remaining populations. The Kruskal-Wallis tests with Bonferroni correction reveals significant differences for these features, with $p<0.0001$, for the five considered brain regions, as visible in FIG. 10. Said figure represents plot boxes of the entropy distribution in the five considered brain regions among the three populations: PD cohort 1, PD cohort 2 and control group.

The invention is not limited to the examples that have just been described.

The invention may be considered for all patients that benefit from deep brain stimulation, often used on patients suffering from Parkinson's disease and known to increase the risks of neurodegenerative decline and cognitive impairment.

The invention claimed is:

1. A method for predicting risks of neurodegenerative decline of a patient, based on at least one medical brain image and at least one clinical and/or biological data of said patient, and using at least a classifier, trained beforehand to learn texture features extracted from a plurality of previously-acquired medical images of one or more areas of the brain and correlated with previously-acquired clinical and/or biological data, the method comprising:
   extracting one or more texture features from said at least one medical brain image to obtain one or more extracted texture features,
   correlating said one or more extracted texture features with said at least one clinical and/or biological data to obtain one or more correlated features, wherein the one or more extracted texture features are correlated with said clinical and/or biological data by using a statistical data modelling technique, and
   based at least on said one or more correlated features, operating the trained classifier on the at least one medical brain image to generate a score representative of the risks of neurodegenerative decline of the patient,
   said score being in the form of a probability for the patient for belonging to a predefined neurodegenerative profile or a predefined cognitive profile, said predefined profiles being used during the learning step of the classifier, in order that the latter can learn to associate the correlated features with such profiles, and/or
   said score being in the form of a numerical value evaluating the risks of neurodegenerative decline at a term of six to 12 months for the patient, and/or
   said score is in the form of a letter showing that the patient is thought to belong to a group of people having a predefined neurodegenerative profile.

2. A method for training a classifier to learn correlated features, the classifier being used in the method for predicting risks of neurodegenerative decline of a patient of claim 1, said training method using a plurality of previously-acquired medical images of one or more areas of the brain and previously-acquired clinical and/or biological data, the method comprising:
   extracting one or more texture features from the previously-acquired medical images to obtain one or more extracted texture features,
   correlating said one or more extracted texture features with at least one of the previously-acquired clinical and/or biological data to obtain correlated features, and
   training the classifier to learn said correlated features.

3. The method of claim 1, wherein the previously-acquired biological data include blood biomarkers, and/or genomic information, and/or histological data.

4. The method of claim 3, wherein the previously-acquired biological data include neural density.

5. The method of claim 1, wherein the previously-acquired clinical data include neuropsychological data.

6. The method of claim 5, wherein the neuropsychological data are scores from MoCA or MMSE neuropsychological tests.

7. The method of claim 1, wherein the previously-acquired clinical data include values measuring a volume of at least one brain structure at different moments.

8. The method of claim 7, wherein, for computing the volume of a brain structure, left and right parts of the brain structure in each hemisphere are segmented for obtaining two bilateral volumes, the volume of the structure being the sum of said bilateral volumes, normalized by the intracranial volume of the brain.

9. The method of claim 7, wherein the values measuring the volume of at least one brain structure are acquired on patients 72 hours after a stroke and six months after a stroke.

10. The method of claim 1, wherein the method is applied in parallel on different brain structures selected from the group consisting of hippocampus, entorhinal cortex, *pallidum*, thalamus, putamen, amygdala, nucleus accumbens, and caudate.

11. The method of claim 10, wherein a sub-region is considered for extraction of the texture features of each structure by extracting a volume of interest.

12. The method of claim 11, wherein the volume of interest is 9×9×9 voxels.

13. The method of claim 10, wherein the texture features extracted from the images include model-based features, including a fractal dimension of the considered brain structure.

14. The method of claim 1, wherein the texture features extracted from the images include first-order statistics selected from the group consisting of mean, standard deviation, kurtosis and skewness.

15. The method of claim 1, wherein the texture features extracted from the images include second-order statistics selected from the group consisting of homogeneity, contrast, entropy, correlation between pixels, variance, sum average, inverse difference moment, and inertia.

16. The method of claim 1, wherein the classifier is a support vector machine or a classification and regression tree.

17. The method of claim 1, wherein, the classifier is a support vector machine, the one or more texture features are extracted for each brain structure and wherein additional features are selected using a Principal Components Analysis.

18. The method of claim 17, wherein, a z-score normalization is applied to the additional features.

19. The method of claim 1, wherein the previously-acquired medical images of one or more areas of the brain and/or the at least one medical brain image are MR images.

20. The method of claim 19, wherein the MR images are T1W images.

21. The method of claim 1, wherein the previously-acquired medical images of one or more areas of the brain are acquired from patients with different neurodegenerative profiles.

22. The method of claim 21, wherein the previously-acquired brain medical images are acquired from healthy patients and/or from patients after a stroke, and/or at different times from patients suffering from Parkinson's disease.

23. Computer program product for predicting risks of neurodegenerative decline based on at least one medical brain image and at least one clinical and/or biological data of said patient, and using at least a classifier, trained beforehand to learn texture features extracted from a plurality of previously-acquired medical images of one or more areas of the brain and correlated with previously-acquired clinical and/or biological data, the computer program product comprising a non-transitory medium and, stored on this non-transitory medium, instructions that can be read by a processor, these instructions being configured to implement the method of claim 1 when executed on a computer.

24. The computer program product of claim 23, wherein the neurodegenerative decline is cognitive impairment.

25. The method of claim 1, wherein the neurodegenerative decline is cognitive impairment.

26. The method of claim 1, wherein the statistical data modelling technique is Pearson correlation, regression and/or ANOVA analysis.

* * * * *